United States Patent [19]
Giannakopoulos et al.

[11] Patent Number: 5,999,887
[45] Date of Patent: *Dec. 7, 1999

[54] METHOD AND APPARATUS FOR DETERMINATION OF MECHANICAL PROPERTIES OF FUNCTIONALLY-GRADED MATERIALS

[75] Inventors: Antonios E. Giannakopoulos, Somerville; Subra Suresh, Wellesley, both of Mass.

[73] Assignee: Massachusetts Institute of Technology, Cambridge, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/805,624

[22] Filed: Feb. 26, 1997

[51] Int. Cl.$^6$ .................................................. G01N 3/42
[52] U.S. Cl. .................................. 702/33; 73/81; 702/41
[58] Field of Search .......................... 364/506; 73/54.02, 73/81, 108, 788; 702/41, 33

[56] References Cited

U.S. PATENT DOCUMENTS

| | | |
|---|---|---|
| 1,071,430 | 8/1913 | Keen . |
| 1,125,912 | 1/1915 | Ringland et al. . |
| 1,348,897 | 8/1920 | Ringland . |
| 3,763,697 | 10/1973 | Sturm .......................................... 73/88 |
| 3,822,946 | 7/1974 | Rynkowski .............................. 356/160 |

(List continued on next page.)

FOREIGN PATENT DOCUMENTS

| | | |
|---|---|---|
| 0 607 466 A1 | 7/1994 | European Pat. Off. . |
| 1260729 A1 | 9/1986 | U.S.S.R. . |
| 1827579 A1 | 7/1993 | U.S.S.R. . |
| 1 481 698 | 8/1977 | United Kingdom . |
| 2 258 536 | 2/1993 | United Kingdom . |
| WO 97/39333 A2 | 10/1997 | WIPO . |

OTHER PUBLICATIONS

Mortensen A. and Suresh, S. Functionally Graded Metal and Metals–Ceramic Composites: Part 1, Processing, International Materials Reviews pp. 1–62 (Sep. 1995).

Bhushan, B and Koinkar, V. Nanoindentation Hardness Measurements Using Atomic Force Microscopy, Appl. Phys. Lett 64(13) pp. 1653–1655 (Mar. 28, 1994).

Soderlund, E and Rowcliffe, D "Analysis of Penetration Curves Produced by Depth–Sensing Indentation Systems" 1994 J. Hard Mater. 5, 149–177 (1994).

National Institute of Standards and Technology (NIST) Special Publication 896: "Conference Preceedings: Internatioall Workshop on Instrumental Indentation", San Diego, CA, Apr. 22–23, 1995, pp. iii–vii, pp. 1–9, and p. 41.

J.S. Field and M.V. Swain, "Determining the mechanical properties of small volumes of material from submicrometer spherical indentations", J. Mater. Res., vol. 10, No.1, Jan. 1995, pp. 101–112.

P.–Larson and A.E. Giannakopoulos, E. Söderlund and D.J. Rowcliffe, and R. Vestergaard, "Analysis of Berkovich Indentation", Int. J. Solids Structures, vol. 33, No. 2, (1996), pp. 221–248.

R. Hill, F.R.S., B. Storåkers and A.B. Zdunek, "A theoretical study of the Brinell hardness test", Proc. Ro. Soc. Lond. vol. A423 (1989), pp. 301–330.

A.E. Giannakopoulos, P.–L. Larsson and R. Vestergaard, "Analysis of Vickers Indentation", Int. J. Solids Structures, vol. 31, No. 19 (1994) pp. 2679–2708.

*Primary Examiner*—James P. Trammell
*Assistant Examiner*—Matthew Smithers
*Attorney, Agent, or Firm*—Wolf, Greenfield & Sacks, P.C.

[57] ABSTRACT

Techniques for the determination of mechanical properties of homogenous or functionally-graded materials from indentation testing are presented. The technique is applicable to indentation on the nano-scale through the macro-scale including the geological scale. The technique involves creating a predictive load/depth relationship for a sample, providing an experimental load/depth relationship, comparing the experimental data to the predictive data, and determining a physical characteristic from the comparison.

27 Claims, 23 Drawing Sheets

U.S. PATENT DOCUMENTS

| | | | |
|---|---|---|---|
| 3,877,298 | 4/1975 | Narang | 73/81 |
| 3,879,982 | 4/1975 | Schmidt | 73/12 |
| 4,023,401 | 5/1977 | Ernst | 73/81 |
| 4,104,901 | 8/1978 | Sidaway | 73/81 |
| 4,275,966 | 6/1981 | Kleesattel | 356/378 |
| 4,277,174 | 7/1981 | Kleesattel | 356/372 |
| 4,304,123 | 12/1981 | Aschinger et al. | 73/81 |
| 4,312,220 | 1/1982 | Borgersen et al. | 73/81 |
| 4,312,221 | 1/1982 | Edward et al. | 73/81 |
| 4,331,026 | 5/1982 | Howard et al. | 73/81 |
| 4,361,034 | 11/1982 | Borgersen et al. | 73/81 |
| 4,372,152 | 2/1983 | Lewis et al. | 73/81 |
| 4,383,450 | 5/1983 | Pringiers et al. | 73/790 |
| 4,463,600 | 8/1984 | Hobbs et al. | 73/81 |
| 4,530,235 | 7/1985 | Shabel | 73/81 |
| 4,535,623 | 8/1985 | Gilberto | 73/81 |
| 4,611,487 | 9/1986 | Krenn et al. | 73/81 |
| 4,621,523 | 11/1986 | Shabel et al. | 73/81 |
| 4,627,096 | 12/1986 | Grattoni et al. | 382/8 |
| 4,653,106 | 3/1987 | Yamatsuta et al. | 382/8 |
| 4,671,104 | 6/1987 | Fischer | 73/81 |
| 4,691,559 | 9/1987 | Fischer | 73/81 |
| 4,699,000 | 10/1987 | Lashmore et al. | 73/81 |
| 4,820,051 | 4/1989 | Yanagisawa et al. | 356/378 |
| 4,852,397 | 8/1989 | Haggag | 73/82 |
| 4,856,326 | 8/1989 | Tsukamoto | 73/150 A |
| 4,896,339 | 1/1990 | Fukomoto | 377/19 |
| 4,945,490 | 7/1990 | Biddle, Jr. et al. | 73/81 |
| 4,956,994 | 9/1990 | Lue | 73/81 |
| 4,984,453 | 1/1991 | Enomoto | 73/81 |
| 5,062,293 | 11/1991 | Bakirov et al. | 73/81 |
| 5,067,346 | 11/1991 | Field | 73/81 |
| 5,133,210 | 7/1992 | Lesko et al. | 73/81 |
| 5,146,779 | 9/1992 | Sugimoto et al. | 73/81 |
| 5,150,608 | 9/1992 | Mazzoleni et al. | 73/81 |
| 5,165,274 | 11/1992 | Thiercelin | 73/151 |
| 5,177,999 | 1/1993 | Tobolski et al. | 73/82 |
| 5,193,383 | 3/1993 | Burnham et al. | 73/105 |
| 5,195,364 | 3/1993 | Dehe et al. | 73/81 |
| 5,284,049 | 2/1994 | Fukumoto | 73/82 |
| 5,309,754 | 5/1994 | Ernst | 73/81 |
| 5,355,721 | 10/1994 | Garcia | 73/82 |
| 5,359,879 | 11/1994 | Oliver et al. | 73/7 |
| 5,365,457 | 11/1994 | Madigosky | 364/506 |
| 5,396,804 | 3/1995 | Moet et al. | 73/788 |
| 5,433,215 | 7/1995 | Athanasiou et al. | 128/744 |
| 5,438,863 | 8/1995 | Johnson | 73/54.02 |
| 5,483,821 | 1/1996 | Mazzoleni et al. | 73/82 |
| 5,486,924 | 1/1996 | Lacey | 356/357 |
| 5,490,416 | 2/1996 | Adler | 73/82 |

METHOD AND APPARATUS FOR DETERMINATION OF MECHANICAL PROPERTIES OF FUNCTIONALLY-GRADED MATERIALS

GOVERNMENT LICENSE RIGHTS

This invention was made with support of the government of the United States of America under grant number DE-FG02-93ER45506 awarded by the U.S. Department of Energy. The U.S. government has certain rights in the invention.

FIELD OF THE INVENTION

The present invention relates generally to measuring mechanical properties of materials, and more particularly to indentation testing from the nano to macro scale for the purpose of measuring physical properties of materials, including functionally-graded materials.

BACKGROUND OF THE INVENTION

The testing of mechanical properties of materials, such as small articles or macro-scale samples such as soil, is a well-studied art. For relatively small-scale articles, standard tests exist for measuring mechanical properties such as Young's modulus, strain hardening exponent, yield strength, hardness, and the like, and the mechanical properties of many materials have been carefully characterized.

One set of techniques for determining mechanical properties in materials involve tests in the macro regime in which, for example, a sample of material is stretched and its overall mechanical response inferred in terms of stress and deformation. These techniques, however, typically are destructive of those samples.

Accordingly, essentially non-destructive techniques for analysis of small-scale samples such as miniaturized semiconductor articles, thin coatings for optical, electronic, magnetic, and mechanical devices, and the like have been developed. Some of these techniques involve in situ testing of mechanical properties in small-scale structures. Properties of individual phases, grain boundaries, and interfaces between phases and properties of novel materials such as nanocrystalline materials, or laminated or fibrous composites have been probed.

Indentation testing is a well-accepted technique for such testing that can be essentially non-destructive, and can be applied at a variety of scales, from nano- to macro-scale. The technique typically involves placing a sample to be tested on a stage and applying a load to a surface of the sample via an indenter so as to slightly deform or penetrate the surface, followed by removal of the load. Several techniques can be employed to derive certain properties of the material from characteristics of the interaction of the indenter with the material. One set of techniques involves measuring an area of indentation during or after indentation, for example, optically, refractively, via surface profilometry, etc. U.S. Pat. Nos. 4,627,096 (Grattoni, et al.), 4,945,490 (Biddle, Jr. et al.), 5,284,049 (Fukumoto), 5,355,721 (Las Navas Garcia), 5,483,621 (Mazzoleni), 5,486,924 (Lacey), 4,852,397 (Haggag), 5,490,416 (Adler), 3,822,946 (Rynkowski), and others follow this procedure. For example, the measured area of indentation can be used to determine a simple "flow" or hardness value for the material, which is defined as the load applied divided by the projected area of the indentation. Or, the dimension of any cracks formed in the sample surface can be measured to determine the toughness of the material. Alternatively, the depth of penetration of the indenter as a function of applied load can be measured, and calculations performed to estimate roughly some mechanical properties.

Various shapes of indenters, for example spherical, cone-shaped, and pyramidal geometries can be used in indentation testing. Sharp indenters (e.g., cone-shaped and pyramidal) can be used in conventional tests to apply a load to a sample surface to form an imprint, or until the surface cracks, followed by measurement of the area of imprint or determination of the crack length to measure hardness or toughness, respectively. One piece of indentation testing equipment utilizing a sharp indenter at ultra low loads is sold by Nano Instruments, Inc. as the Nanoindenter™ indentation tester. The Nanoindenter™ indentation tester is a relatively complex, self-contained unit including an indenter system, a sharp indenter, a light optical microscope, a moveable x-y table, and a computer. Analysis of load/depth curves with loads of less than one Newton and displacement of less than one $\mu$m using a three-sided pyramidal indenter is most typically performed.

Blunt indenters, for example those having a surface contacting the sample surface that is spherical, are advantageous for use in indentation testing under certain circumstances for several reasons. First, less sample-destructive analyses often can be carried out. However, with blunt (spherical) indenters, sensitivity problems are maximized since displacement of the sensor into the sample surface, at a particular applied load, is less than displacement with a sharp indenter. This is especially problematic in measuring very soft materials. Spherical indenters have, therefore, found most use in techniques in which load is applied to a sample surface and the diameter of the indentation formed thereby is measured using, for example, optical means.

A variety of U.S. Patents, including U.S. Pat. Nos. 4,820,051 (Yanagisawa, et al.); 4,627,096 (Gattoni, et al.); 4,699,000 (Lashmore, et al.); 5,133,210 (Lesko, et al.); 5,490,416 (Adler); and 4,852,397 (Haggag) describe techniques that involve indenting a sample and determining, in a variety of ways, load, depth of penetration, and/or area of contact between the indenter and the sample during the test. In some cases an optical mechanism determines the penetration depth of the indenter and/or the area of contact between indenter and sample. In some cases, during determination of area of contact, it is assumed for simplicity that no pile-up or sinking-in of the material at the contact perimeter occurs (which is known to be a factor that must be taken into account for accurate measurement). Typically, in these techniques, the area of the indentation formed while load is applied either is not made precisely, or requires relatively complicated apparatus. In some cases, relatively time-consuming and labor-intensive processes are carried out involving multiple indentation tests made where the profile of the indentation is traced after each test with a surface analyzer to determine the depth and diameter of the indentation.

Accurate determination of the area of an indentation formed during indentation testing, especially during loading, can be critical to accurate determination of several mechanical properties of a sample. Most of these techniques also cannot accurately determine properties of a sample in the elastic and plastic regimes within a single test.

Co-pending, commonly-owned, U.S. patent application Ser. No. 08/632,665, of Suresh, Alcala, and Giannakopoulos, filed Apr. 15, 1996 and entitled, "DEPTH SENSING INDENTATION MECHANISM AND METH- ODOLOGY FOR MECHANICAL PROPERTY MEASUREMENTS, describes an improved technique allowing simple, reproducible, relatively uncomplicated, inexpensive, and accurate measurement of a variety of mechanical properties in a single test or series of tests on homogeneous materials. The technique involves deriving, from a load/depth relationship from an indentation test, an area of contact between the indenter and the sample during penetration without observing the area of contact during or after penetration. The area determined takes into account the area of contact due to pile-up of sample material around the indenter or sinking-in of the material. In situ load/displacement measurement, using a variety of indenter shapes and sizes, is possible in this technique.

The above techniques provide useful data for a variety of purposes, for homogeneous materials but not for functionally graded materials. Yet simplification of testing of a variety of materials at a variety of size scales would be advantageous. Accordingly, it is an object of the present invention to provide a simplified technique for indentation testing that is accurate, and is applicable to a wide variety of materials, over a variety of size scales.

SUMMARY OF THE INVENTION

The present invention enables characteristics of a functionally-graded material to be measured using indentation testing. In particular, one aspect of the present invention is performing an indentation test on a sample with an indenter in a direction essentially parallel to a direction of gradation of a functionally-graded material and deriving and recording a relationship between the load applied to the indenter and the depth of penetration of the indenter into the sample.

Another aspect of the invention is a process for generating digital information indicative of a measure of variation of a mechanical property of a material. Signals indicative of a load/depth relationship from an indentation test are received for at least two depths of an indenter applied to the material. Input indicative of the geometry and properties of the indenter and Poisson ratio of the material are also received. The variation in the mechanical property is computed as a function of the load/depth relationship, the geometry of the indenter, and the Poisson ratio. In one embodiment, when the variation is essentially zero, the material is a homogeneous material. In another embodiment, when the variation is non-zero, the material is a functionally-graded material. The computation may use a known reference value of the mechanical property at a reference location in the sample, such as the elastic modulus.

Another aspect of the invention is a process for measuring a mechanical property of a functionally-graded material. Signals indicative of a load/depth relationship of an indentation test are received for at least two depths of an indenter applied to the material. Signals indicative of the geometry and properties of the indenter and Poisson ratio of the material are also received. The mechanical property is computed as a function of the load/depth relationship, the geometry of the indenter, and the Poisson ratio. In one embodiment, the variation in the mechanical property is computed as a function of depth, geometry, and Poisson ratio of the sample. The computation may make use of a known reference value of the variation in the mechanical property, such as the elastic modulus.

Another aspect of the invention is a process for detecting a deviation from a variation in a mechanical property of a material as a function of depth. Signals indicative of a load/depth relationship of an indentation test are received for a depth of an indenter applied to the material. Signals indicative of the geometry of the indenter and a Poisson ratio of the material also are received. A load/depth relationship is computed according to the geometry and properties of the indenter, the Poisson ratio, and the variation in the mechanical property and a reference mechanical property. The computed load/depth relationship is compared to the received signal to detect the deviation. The variation may be known, or predetermined. The variation may be determined by computing the variation in the mechanical property as a function of the load/depth relationship, the geometry of the indenter, and the Poisson ratio. The reference mechanical property also may be computed as a function of the load/depth relationship, the geometry of the indenter, and the Poisson ratio.

Other advantages, novel features, and objects of the invention will become apparent from the following detailed description of the invention when considered in conjunction with the accompanying drawings.

Figure 1:
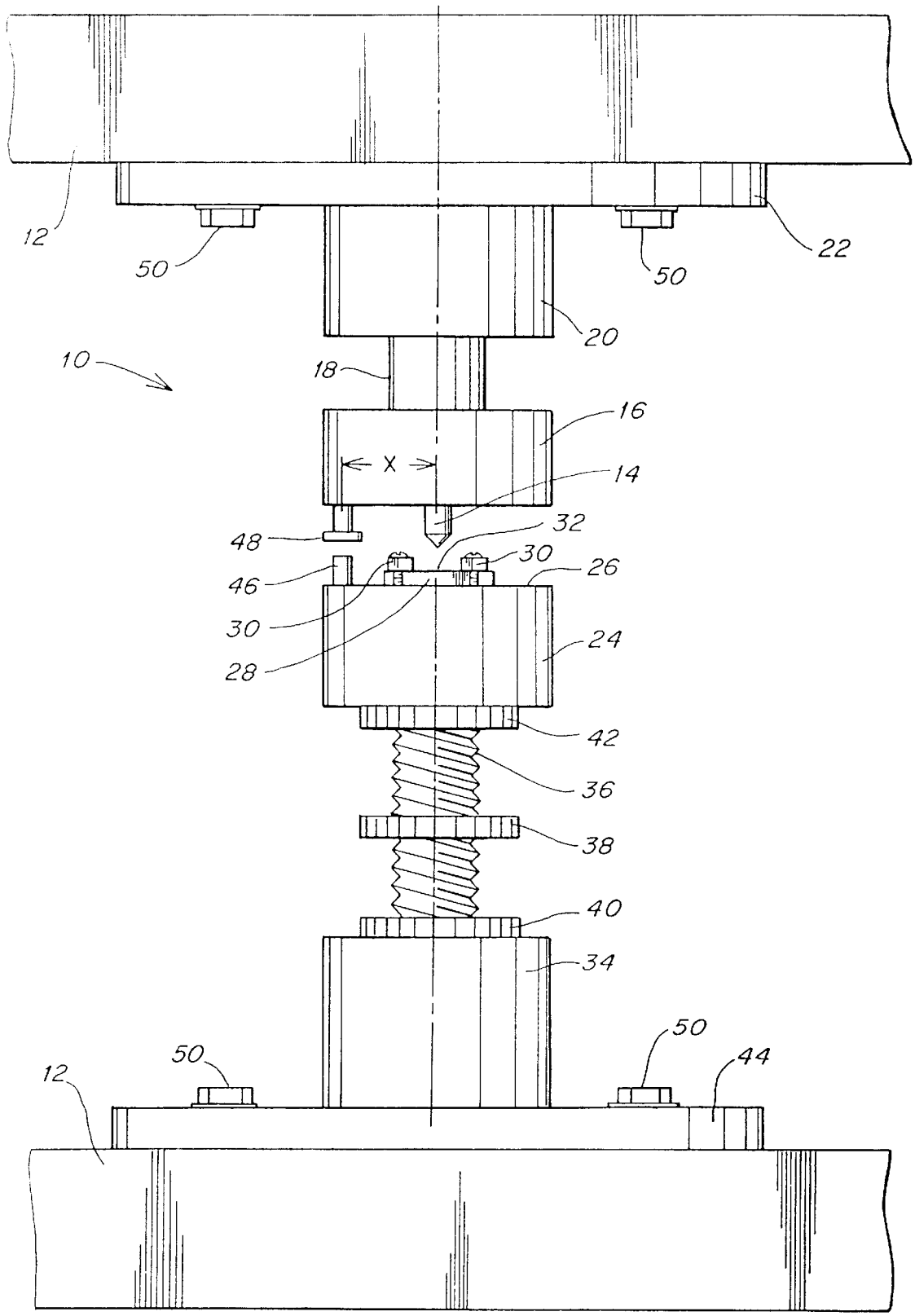
FIG. 1 is an elevational view of an indenter apparatus with which the present invention may be used.

NOMENCLATURE a: contact radius
A: contact area of an indenter
c: volume fraction of the constituent phase of the graded layer
D: diameter of a spherical indenter
$E_{surf}$: Young's modulus of the indented surface
$E_{subs}$: Young's modulus of the homogeneous substrate
Eo: Young's modulus of sample at reference depth, e.g., z=0 for exponential model and z=1 for power law model.
$E_{ind}$: Young's modulus of the indenter
$E_{spec}$: corrected specimen's reference modulus
K: combined effective Young's modulus (indenter and sample)
h: measured depth of an indenter relative to the surface of a sample (penetration; displacement)
P: load applied to sample via an indenter
X: distance between the displacement sensor and the axis of an indenter
z: depth coordinate
$v_o$: Poisson ratio of sample
$v_{ind}$: Poisson ratio of the indenter
$V_{spec}$: corrected specimen's Poisson ratio
$h_{tot}$: total indentation depth that includes indenter/anvil compliance
$C_{ind}$: compliance between indenter and anvil
α: variation coefficient
P': load predictor
Δα: increment of α

$$\frac{dp}{dh}\bigg|1, \frac{dp}{dh}\bigg|2:$$

slopes of the P-H curve at points 1, 2, respectively
$a_1, a_2$: contact radii at two loading points 1, 2, respectively
b: parameter of the power law model
ψ: parameter of the exponential law model
2γ: angle of the conical indenter
Γ: gamma special function
C: indentation compliance of the material

DETAILED DESCRIPTION OF THE INVENTION

The present invention provides techniques associated with indentation testing for deriving information about mechanical properties of a sample of material without the requirement of observing or determining the area of contact between indenter and sample, or observing or determining morphological changes to the material as a result of indentation. The invention involves predicting certain unknown properties of a material, generating predictive load/depth data for the material, providing measured load/depth data of the material, comparing the predictive data to the measured data, and determining physical characteristics of the material. One particularly useful aspect of the invention is its applicability to indentation testing of functionally-graded materials.

"Indentation testing", as used herein, can involve measurement in situ with known indentation apparatus, or apparatus as described in the above-referenced application Ser. No. 08/632,665, of Suresh, et al., using blunt (spherical or rounded tip) and sharp indenters (such as those having cone or pyramidal geometries, commonly referred to as Rockwell, Vickers or Berkovich indenters), by monitoring the penetration of an indenter into a polished specimen over a range of applied loads. In certain applications, e.g., geomechanics, a flat punch may be used. Additionally, indentation with a drill or press, including large-scale indentation such as with a pile driver or auger as used in construction of large buildings, is included in this definition for purposes of the invention. Fundamental mechanical properties relating to elasticity (and plasticity) can be obtained from techniques of the invention.

Referring to FIG. 1, one example of an indentation testing apparatus that can be used in connection with the present invention is illustrated schematically. FIG. 1 illustrates indentation testing apparatus described in the above-referenced U.S. patent application Ser. No. 08/632,665 of Suresh, et al. It is to be understood that this arrangement is provided for purposes of illustration only, and is not intended to be limiting. Indentation testing apparatus 10 can be mounted in an existing laboratory load-applying frame 12. Apparatus 10 is axisymmetric, that is, symmetric about the axis of loading, and includes an upper, indenter-carrying portion and a lower, sample-carrying portion. The upper portion includes an indenter assembly 14 mounted securely on an indenter mount 16 which is fastened to a load cell 18, which is in turn fastened to an upper mount 20 including an upper flange 22 adapted to be secured to the load-applying frame. The lower, sample-carrying portion includes a fixture 24, a top, or stage surface 26 of which defines a stage upon which a sample 28 is positioned for testing, and against which the sample can be securely held with one or more clamps, or brackets 30. The apparatus is arranged such that the indenter is positioned above a top surface 32 of sample 28. Top surface 32 can be polished prior to analysis.

Fixture 24 is secured to a base support 34 by, for example, a threaded adjusting mount 36 that threads into fixture 24 and/or base support 34. Adjusting mount 36 is preferred, but not necessary. Fixture 24 can be secured directly to (or be integral with) base support 34. As illustrated, a rotation grip 38 allows rotation of threaded adjusting mount 36, a lock nut 40 threaded on mount 36 can secure threaded adjusting mount 36 via frictional engagement with base support 34, and a lock nut 42 threaded on mount 36 can secure threaded adjusting mount 36 via frictional engagement with fixture 24. This arrangement allows for rotation of threaded adjusting mount 36 about a vertical axis to adjust the distance between indenter assembly 14 and sample surface 32, and independent adjustment of the rotational orientation of stage surface 26 and sample 28 so that sensor 46 and mirror 48 (discussed below) can be aligned. As discussed below, a displacement sensor can also be adjusted independently. Base support 34 includes a lower flange 44 adapted to be secured to load-applying frame 12.

A displacement sensor 46 can be provided to measure displacement of an indenter carried by indenter apparatus 14 relative to a surface 32 of sample 28 that is probed by the indenter. Displacement sensor 46 can be associated with fixture 24 or indenter mount 16 and, as illustrated, the sensor is an optical sensor mounted on stage surface 26, and a corresponding mirror 48 is mounted on indenter mount 16. Optical displacement sensors, for example a combination photonic probe and photonic sensor sold by Photonics, Inc, are known. Equivalent displacement sensors, e.g., capacitors, magnetic coils, or linear variable differential transformers of similar resolution are acceptable according to this embodiment. Mirror 48 is positioned so as to reflect light emitted by sensor 46 back to the sensor. In this manner the sensor can determine the displacement of the indenter relative to surface 32 of sample 28. The sensor operates via a standard technique by which the variation of intensity between the emitted and received light is used to measure the relative motion between the probe and mirror 48 (thus displacement of the indenter relative to surface 32 of sample 28).

The vertical position of mirror 48 relative to indenter mount 16 can be adjusted, for example via a threaded coupling and lock nut, or via slidable engagement and screw (not shown). In this manner the position of mirror 48 relative to optical sensor 46 is adjustable to achieve optimal distance therebetween for measurement of penetration into the sample. Additionally, the distance between the indenter assembly 14 and surface 32 of sample 28 can be decreased at a controlled rate by adjusting the loading frame within which the system is positioned (described more fully below).

When a load is applied to surface 32 of sample 28 via the indenter, the applied load is measured with load cell 18, and in conjunction with optical sensor 46, a load/displacement curve can be obtained, both upon loading and unloading of the sample. The optical sensor 46 measures the depth of penetration of the indenter of indenter assembly 14 into surface 32 of sample 28 with great accuracy. The load cell 18 has high resolution, and can apply any of a wide variety of loads, and the apparatus can be equipped to conduct indentation tests within any of a wide range of loads.

The diameter of the indentation made is preferably less than about 1/5 of the smallest diameter of the specimen (lateral dimension or height), in homogeneous materials. For layered materials, indentation depth should be less than about one-tenth of the thickness of the layer sampled to obtain properties of the layer, or greater than the thickness to obtain properties of the substrate.

Apparatus 10 can provide particularly accurate measurement via a combination of stiffness and arrangement of the overall indenter apparatus, as described more fully in application Ser. No. 08/632,665. The normality of movement of the indenter relative to surface 26 of fixture 24 can be within a prescribed, narrow range. The stiffness of the apparatus is advantageous in that it can be retrofitted into essentially any load-applying laboratory apparatus.

Flange 22 of upper mount 20 and flange 44 of base support 34 each are bolted to frame 12 (described below) with bolts 50 that each pass through their respective flange and are threaded into frame 12. This is described more fully below with reference to FIG. 2.

Preferably, all components of apparatus 10 (with the exception of, e.g., mirror 48, displacement sensor 46, and the indenter) are made of stainless steel.

Figure 2:
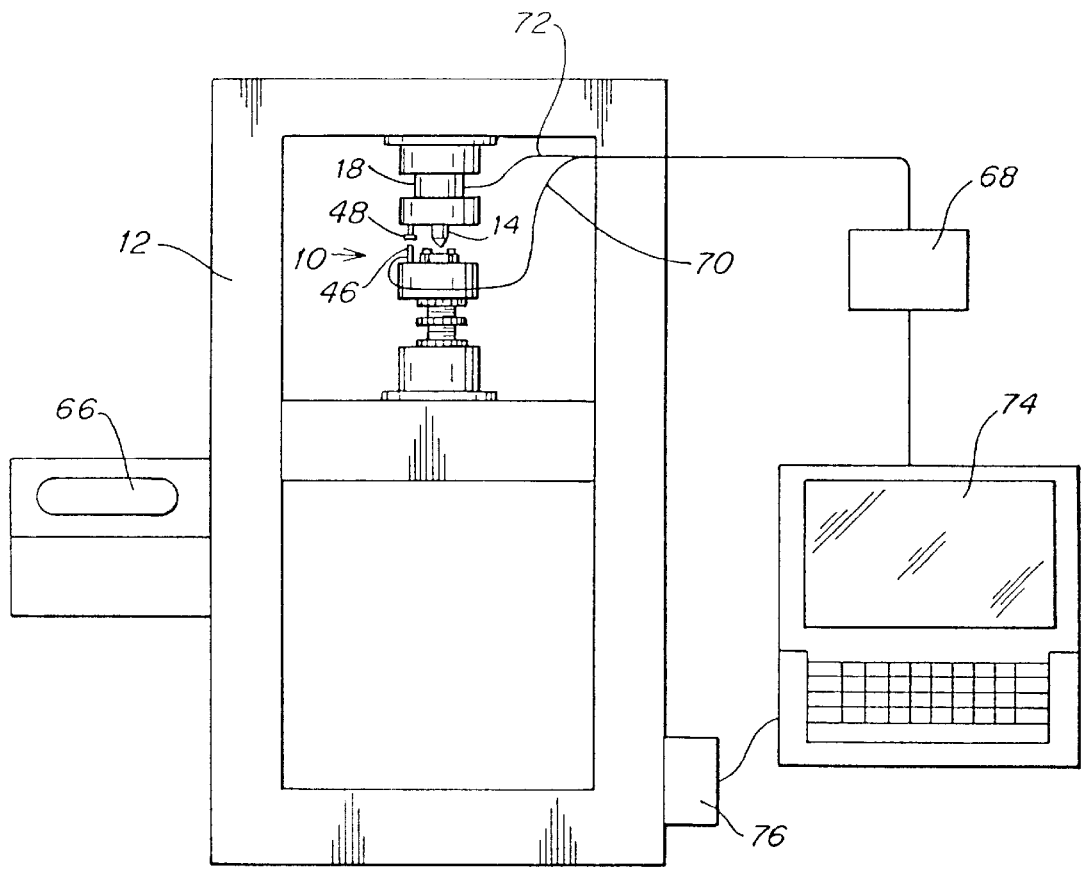
FIG. 2 is an illustration of how an indenter apparatus as shown in FIG. 1 may be connected to a computer.

Illustrated in FIG. 2 is equipment that allows automated testing of a sample and automated analysis of data obtained from indentation testing. A control panel 66 can be used to manually control the loading frame 12, and load applied. A fast D/A converter 68 is connected via a lead 70 to displacement sensor 46 and via a lead 72 to load cell 18 so as to acquire load and indentation depth measurements via a computer 74. LABVIEW software, for example, can be used for data acquisition. Testing parameters, such as maximum load and indenter type, are fed into the computer 74 which then directly acquires the data via the D/A converter and controls the test by standard general purpose interface bus (GPIB) connections 76. The computer 74 also can be arranged to control an X-Y stage (not shown) upon which the specimen can be mounted, and other adjustable components such as mirror 48 so that an entire set-up and testing procedure is essentially automated, and indentations can be performed at pre-selected locations serially.

Figure 3:
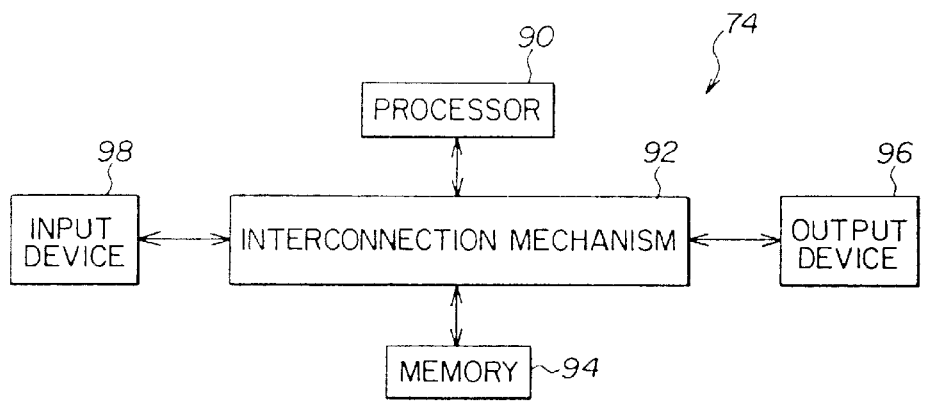
FIG. 3 is a block diagram of an example computer system which may be used in one embodiment of the present invention shown in FIG. 2.

An example computer system 74 is in FIG. 3. The computer 74 generally includes a processor 90 connected to a memory 94 via an interconnection mechanism 92. An input device 98 is also connected to the processor and memory system via the interconnection mechanism, as is an output device 96.

It should be understood that one or more output devices 96 may be connected to the computer 74. Example output devices include cathode ray tube (CRT) displays, liquid crystal displays (LCD), printers, additional storage devices and control outputs via the GPIB connections 76, communication devices such as a modem. It should also be understood that one or more input devices 98 may be connected to the computer 74. Example input devices include GPIB connections 76, a keyboard, keypad, track ball, mouse, pen and tablet and communication device. It should be understood the invention is not limited to the particular input or output devices used in combination with the computer 74 or to those described herein.

The computer 74 may be a general purpose computer system which is programmable using a high-level computer programming language, such as "C," "Pascal" or "Visual Basic." The computer may also be specially programmed, using special purpose hardware. Additionally, the computer 74 may be a multiprocessor computer system or may include multiple computers connected over a computer network.

In a general purpose computer system, the processor 90 is typically a commercially available processor, of which the series×86 processors, available from Intel, and the 680X0 series microprocessors available from Motorola are examples. Many other processors are available. Such a microprocessor executes a program called an operating system, of which UNIX, DOS and VMS are examples, which controls the execution of other computer programs and provides scheduling, debugging, input/output control such as for the GPIB connections, accounting, compilation, storage assignment, data and memory management, communication control and related services. The processor and operating system define a computer platform for which application programs in various programming languages may be written. It should be understood the invention is not limited to a particular computer platform, particular processor, or particular high-level programming language.

Figure 4:
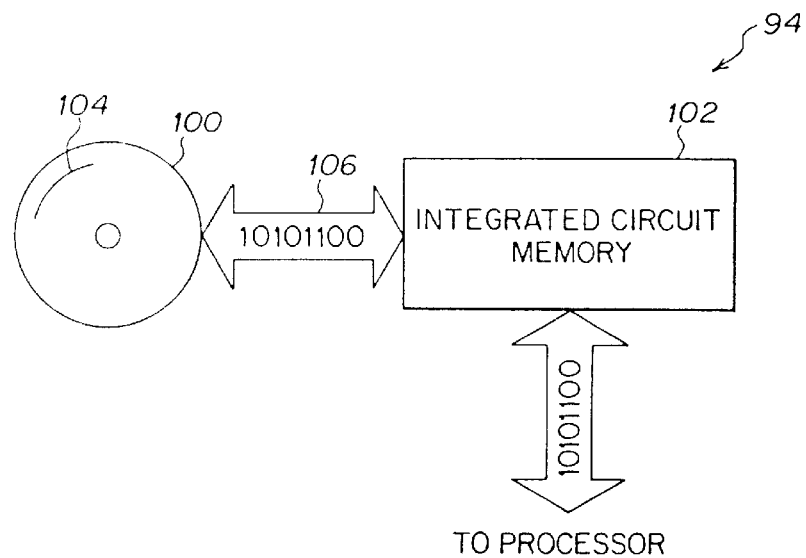
FIG. 4 is a block diagram of a memory system shown in FIG. 3.

An example memory system 94 will now be described in more detail in connection with FIG. 4. A memory system typically includes a computer readable and writeable nonvolatile recording medium 100, of which a magnetic disk and tape are examples. The disk may be removable, known as a floppy disk, or permanent, known as a hard drive. Where the medium 100, a disk, which is shown in FIG. 4, has a number of tracks, as indicated at 104, in which signals are stored, typically in binary form, i.e., a form interpreted as a sequence of one and zeros such as shown at 106. Such signals may define an application program to be executed by the microprocessor, or information stored on the disk to be processed by the application program. Typically, in operation, the processor 90 causes data to be read from the nonvolatile recording medium 100 into an integrated circuit memory element 102, which is typically a volatile, random access memory such as a dynamic random access memory (DRAM) or static memory (SRAM). The integrated circuit memory element 102 allows for faster access to the information by the processor than does the medium 100. The processor generally manipulates the data within the integrated circuit memory 102 and then copies the data to the medium 100 when processing is completed. A variety of mechanisms are known for managing data movement between the medium 100 and the integrated circuit memory element 102, and the invention is not limited thereto. It should also be understood that the invention is not limited to a particular memory system 94.

Using a system such as described above in connection with FIGS. 1 through 4, it is possible to analyze a material using indentation to determine some of its mechanical properties. A wide variety of samples such as metals, oxides, carbides, ceramics, glasses, polymers, composites, layered solids such as surface coatings, and similar materials can be analyzed. The methodology and apparatus of the invention can be applied to locally isotropic, inhomogeneous, elastic and elasto-plastic materials at room temperature. The material may be transversely non-isotropic. The Poisson ratio may be constant, or, if variable, the variation should be known and an average value should be determined.

In one set of embodiments, determination of properties of functionally-graded materials is made, including articles comprised of a combination of the above and/or other materials. "Functionally-graded" materials, as used herein, include those that change, as a function of depth, in terms of any physical property. Functionally-graded materials include those that change in terms of ratio of materials, change in molecular weight, change in density (porosity), or the like as a function of depth by, for example, differential thermal treatment during fabrication, ion or electron bombardment, controlled, graded deposition, material structural orientation, or the like. Intentionally-graded materials that are fabricated as such, and unintentionally-graded materials such as samples that change as a function of depth due to natural material diffusion over time, are included. Many natural products, such as soil, stone, bone, teeth, etc. are functionally-graded.

In addition to many research-type applications, the present apparatus and methodology can be used in routine industrial practice in inspection of materials, potentially non-destructively, such as metallurgical operation on alloys (e.g., carborizing, quenching, tempering, nitriding, case-hardening, and annealing) as well as to study variation of chemical composition (e.g., through diffusion). The methodology can be used in a wide variety of geological tests such as those performed in connection with the construction of foundations of buildings, excavations or other earth works.

The invention finds use with functionally-graded materials that are graded, as a function of depth, essentially continuously. "Essentially-continuously-graded", as used herein, means material that is graded and that changes according to any monotonic function as a function of depth, for example material that changes linearly or exponentially, and does not include significant discontinuity. In particular essentially-continuously-graded materials include those in which the deviation from continuity (e.g. the size of strata in a stratified material) is much less than the contact area between indenter and sample. Preferably, the indenter/sample area of contact is greater than about 5 times the size of strata in stratified material, and the variation of a particular property between adjacent strata is less than about 10% of a reference value, typically the value at the surface of the sample.

The invention involves, according to preferred embodiments, determination of mechanical properties of a material from the indentation test, such as Young's modulus (E) from the unloading portion of a load/displacement curve where a sharp indenter is used and/or from the initial portion of the load/depth measurement as well as from unloading using a blunt indenter such as a spherical indenter. In some cases, the load/displacement curve and the contact area are observed. For unloading tests, the load/displacement data for unloading for at least two different depth levels and the contact area are observed. In one embodiment, the area of an imprint from an indentation test of a functionally-graded material is obtained directly from load/displacement measurement. The load/depth information provided from an indentation test may be analyzed by the computer associated with the indentation equipment, or the raw measurements may be stored and analyzed at a later time and/or different location. Spherical indentation is recommended. Several mechanical properties can be determined in a single load/unload cycle, and accuracy of determination of several properties can be assessed by comparison between analyses using different indenter geometries.

Where it is desirable to determine the area of contact between indenter and sample, in some cases an imprint formed during indentation testing can be observed visually or, in some cases, can be derived without the need for visual or other measurement, as described in co-pending, commonly-owned, U.S. patent application Ser. No. 08/632, 665, of Suresh, Alcala, and Giannakopoulos, filed Apr. 15, 1996 and entitled, "DEPTH SENSING INDENTATION MECHANISM AND METHODOLOGY FOR MECHANICAL PROPERTY MEASUREMENTS," incorporated herein by reference.

A functionally graded material will have an elastic modulus (E) that varies with the depth of the material according to a variation $\alpha$ and a function that can be approximated by a power law equation or an exponential law equation. The linear variations with depth can also be extracted. Graphs illustrating the variation in Young's modulus as a function of depth according to the exponential model equation and the power law model equation are shown in FIGS. 5 and 6 respectively.

Figure 5:
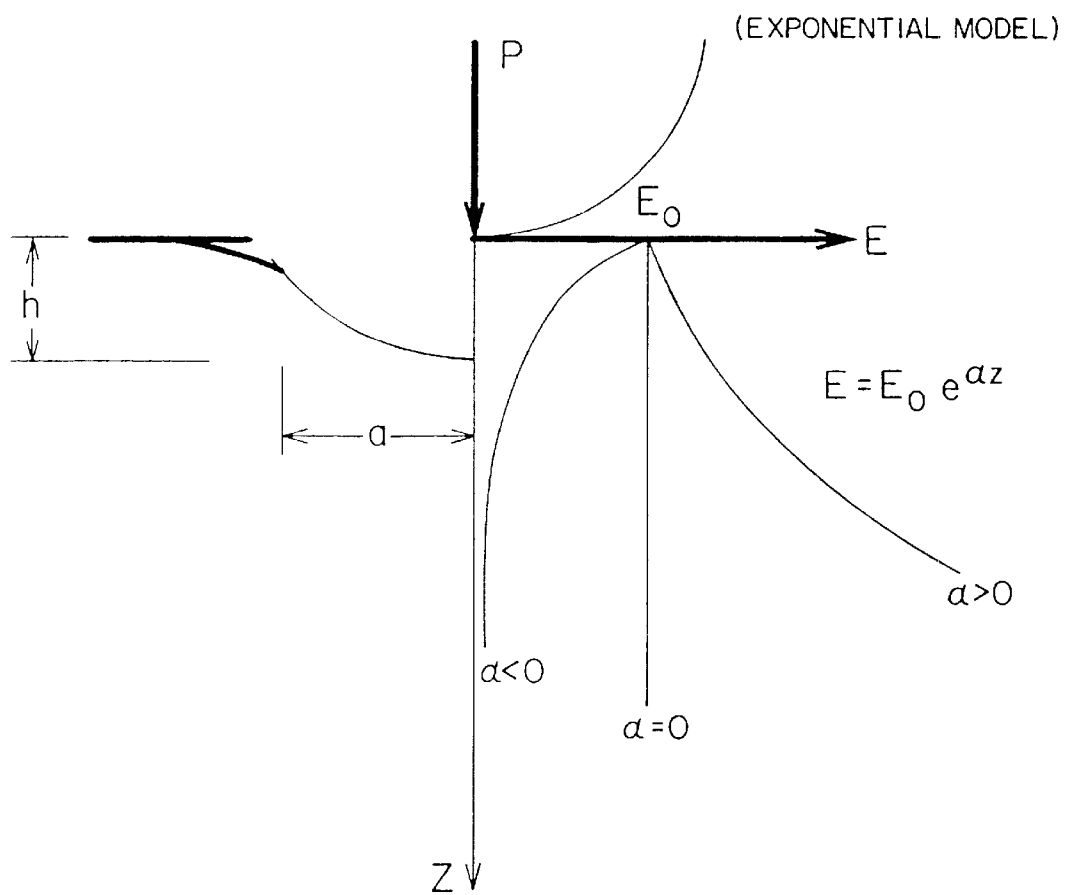
FIG. 5 is a graph of the Young's modulus with respect to depth in a functionally-graded material, wherein the variation in Young's modulus follows an exponential law.

Referring now to FIG. 5, for materials that follow an exponential model, at given load P, the indenter will cause a displacement to a depth h, and have a contact area a. The value of h at a given load P will be a function of the elastic (Young's) modulus, which in a functionally graded material that follows the exponential model, will vary as a function of depth according to the following equation: $E = E_o e^{\alpha z}$ As a result, if the value of the variation $\alpha$ is less than zero, the material is softer below the surface. The material is harder below the surface if the variation α is greater than zero. The material is homogeneous if there is no variation. In this embodiment, Eo is the representative elastic modulus at the surface of the material, i.e., where z=0.

Figure 6:
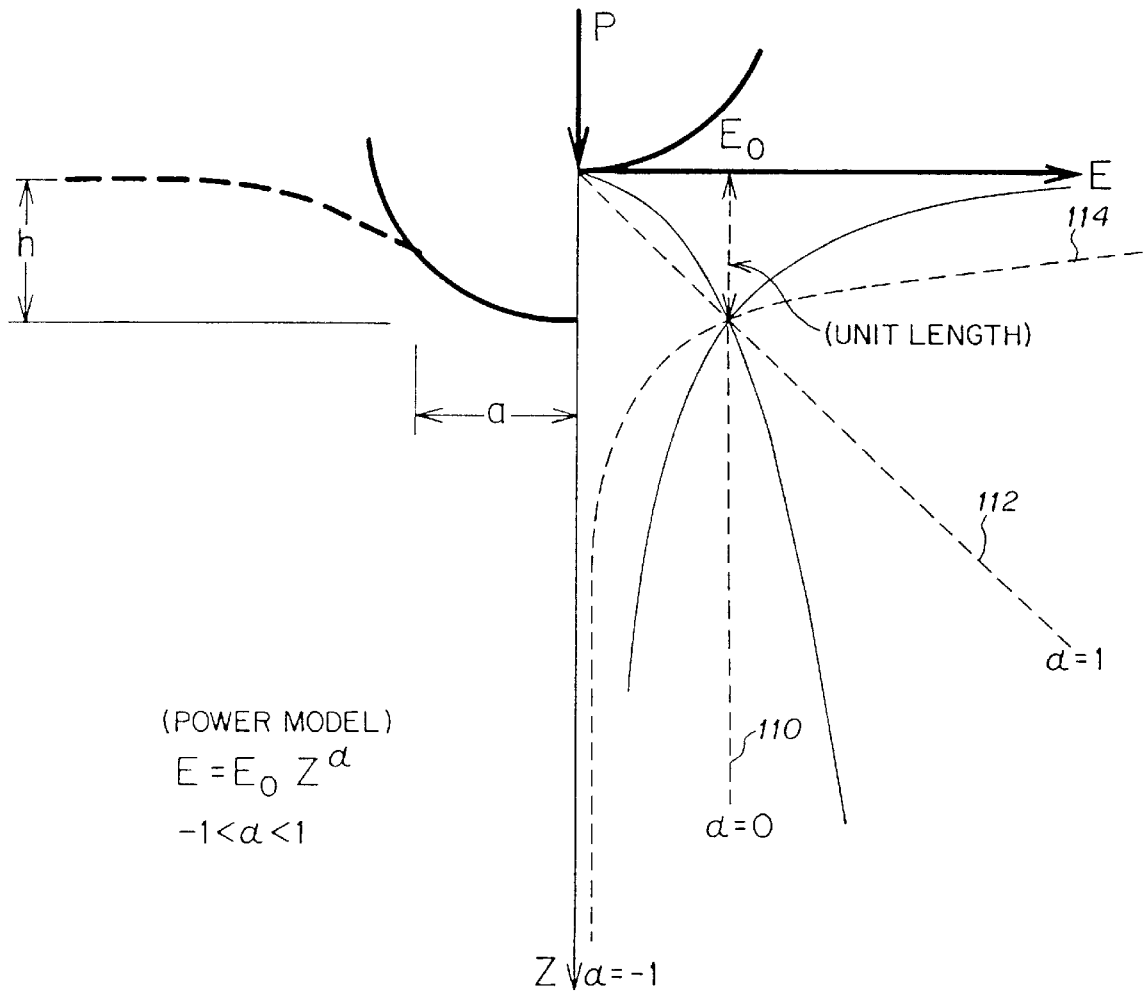
FIG. 6 is a graph of the Young's modulus with respect to depth in a functionally-graded material, wherein the variation in Young's modulus follows a power law.

Referring now to FIG. 6, for materials that follow a power law model, at given load P, the indenter will cause a displacement to a depth h, and have a contact area a. The value of h at a given load P will be a function of the elastic (Young's) modulus, which in a functionally graded material that follows the power law model, will vary as a function of depth according to the following equation: $E=E_o z^\alpha$, where $-1<\alpha<1$. Line 110 illustrates the case where α=0. Line 112 illustrates the case where α=1. Line 114 illustrates the case where α=1. If the value of the variation α is less than zero, the material is softer below the surface. The material is harder below the surface if the variation α is greater than zero. The material is homogeneous if there is no variation. In this embodiment, Eo is the representative elastic modulus at the surface of the material, i.e., where z=1, or, a unit length selected by the investigator and should be within twice the contact radius a.

In both of the cases, i.e., using the exponential model or the power law model, the Young's modulus Eo should be greater than 0. The Poisson ratio is assumed to be known, and is typically greater than or equal to zero, and less than 0.5.

While the actual elastic variation in a material can be different from either of these models, these models provide suitable approximations where the variation is continuous and monotonic to a depth of about three times the constant radius of the indentation area. These analytical models contain enough information to permit extraction of Young's modulus Eo and its variation α. The method is simplified if some prior knowledge about the type of model (whether power or exponential) is available, or if Eo or α is known. In many cases, Eo will be known. In the most general case, both the power and exponential law models should be used. The best matching curve is selected as the appropriate model.

Given the load/depth curve from an indentation test, the elastic modulus and variation can be determined automatically, as will now be described in connection with FIGS. 7 through 21. Before this processing is performed, the penetration due to possible compliances, such as in an indentation test that uses a spherical indenter, should be accounted for by subtracting this out of the load/depth data received from the indenter. In particular, $$h_{tot}=(P/C_{ind})^{2/3}+h$$

Figure 7:
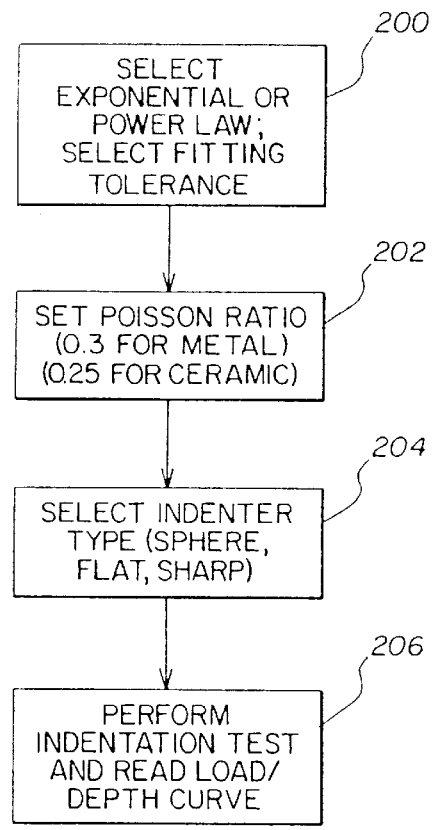
FIG. 7 is a flowchart describing how an indentation test is performed to enable evaluation of mechanical properties in accordance with the invention.

Referring now to FIG. 7, the process begins with a user selecting several characteristics for the tests. First, the user selects a model step 200 which the characteristics of the material are expected to follow, such as either the exponential or power law models, or both. Both models would be selected if nothing is known about the material. A tolerance value, typically less than 0.05, is also selected. In step 202, the user then sets a value for the average Poisson ratio. This is typically 0.3 for metals and 0.25 for ceramics. The Poisson ratio is assumed to be fixed in the graded material. However, variations in the Poisson ratio of up to about 10% of the average do not change significantly the results. This value can be set to any value that seems most realistic for the type of material involved. The user then selects the type of indenter and provides an indication of this selection to the computer in step 204. There are several types of indenters which are generally characterized as spherical, sharp, or flat.

Sharp indenters include triangular and square pyramids and cones, whereas flat indenters may have a circular, square or other shape.

Next, in step 206, the actual indentation test is performed resulting in a load/depth (P-h) curve. In these measurements, the depth value should be measured from the material surface and should account for internal compliance of the indentation apparatus, particularly for spherical indenters. Step 206 may involve reading a load depth curve during loading for a spherical indenter. For indention tests involving sharp or flat punches at least two load/depth curves and corresponding contact areas are measured for unloading tests on elastic or elastoplastic materials. For elastoconical indentations, the load/depth curve of a loading test may be used.

Figure 8:
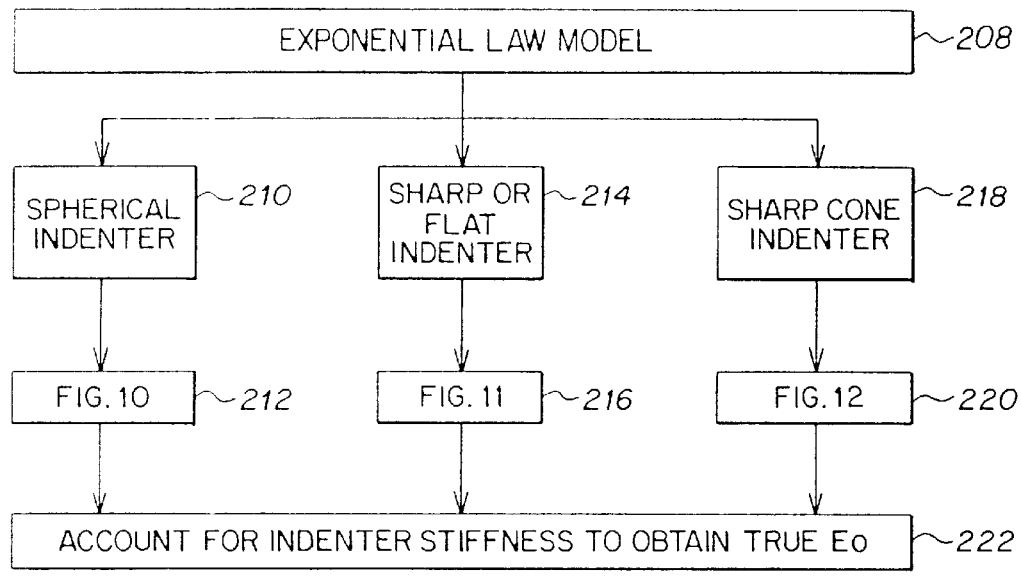
FIG. 8 is a flowchart describing the selection of procedures for evaluating mechanical properties according to a type of indenter used using an exponential law model.

Given the received test data and other measures from the user, the Young's modulus and the variation of the Young's modulus with depth are then determined according to the model selected by the user. If an exponential law model was selected, as illustrated in FIG. 8 at step 208, there are three possible ways to determine these characteristics depending on the type of indenter. Given a spherical indenter, as noted at 210, these values are determined in step 212 in a manner to be described below in more detail in connection with FIG. 10. For a sharp or flat indenter, as indicated at 214, these values are determined as indicated at 216, according to FIG. 11. For sharp cone indenters, as indicated at 218, the values are determined at step 220 in accordance with FIG. 12. The resulting values for Young's modulus are then adjusted to account for indenter stiffness to provide the true Young's modulus of the material, as indicated at 222, as will be described in more detail below.

Figure 9:
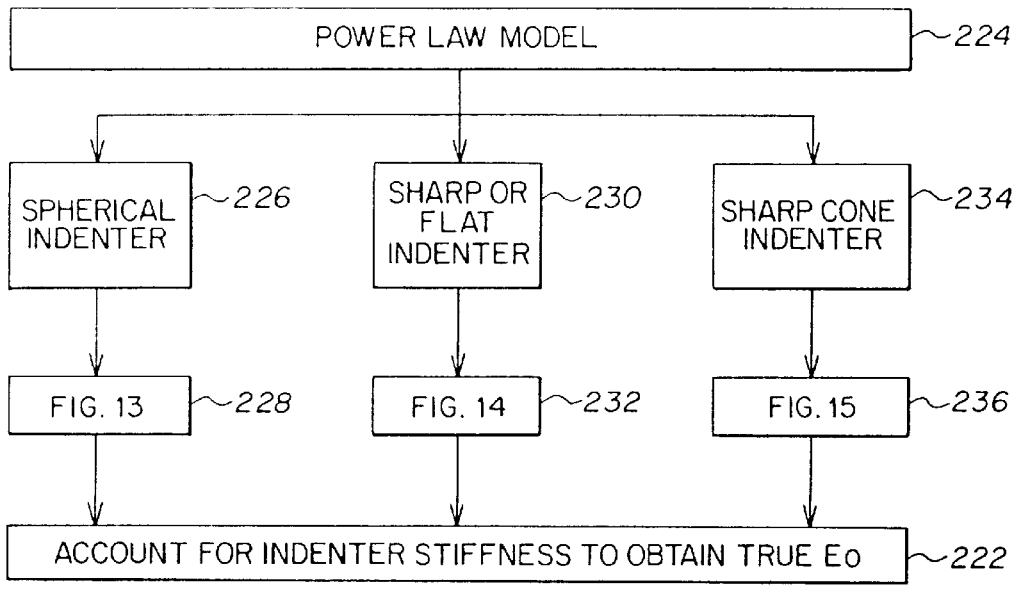
FIG. 9 is a flowchart describing the selection of procedures for evaluating mechanical properties according to a type of indenter used using a power law model.
Figure 13:
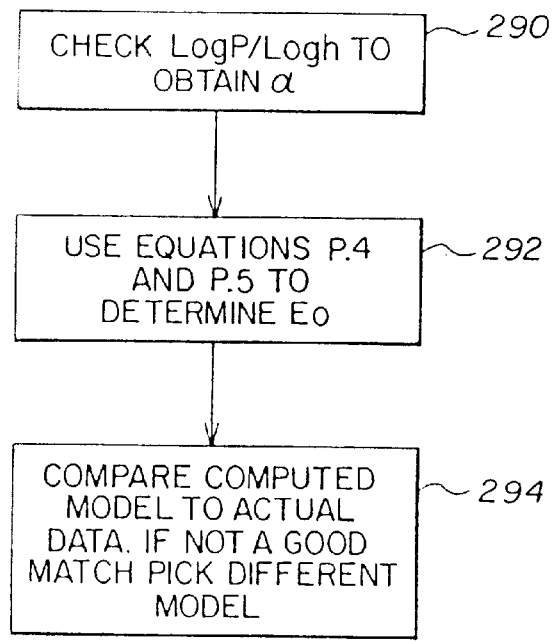
FIG. 13 is a flowchart describing how mechanical properties are determined using a power law model, for a spherical indenter.

Referring to FIG. 9, if the power law model is selected as indicated at 224, and if the indenter is spherical as indicated at 226, the values are calculated at step 228 in accordance with FIG. 13. For sharp or flat indenters, as indicated at 230, these values are determined at step 232 in accordance with FIG. 14. For sharp cone indenters as indicated 234, these values are determined in step 236 as will be described in more detail below in connection with FIG. 15.

Figure 10:
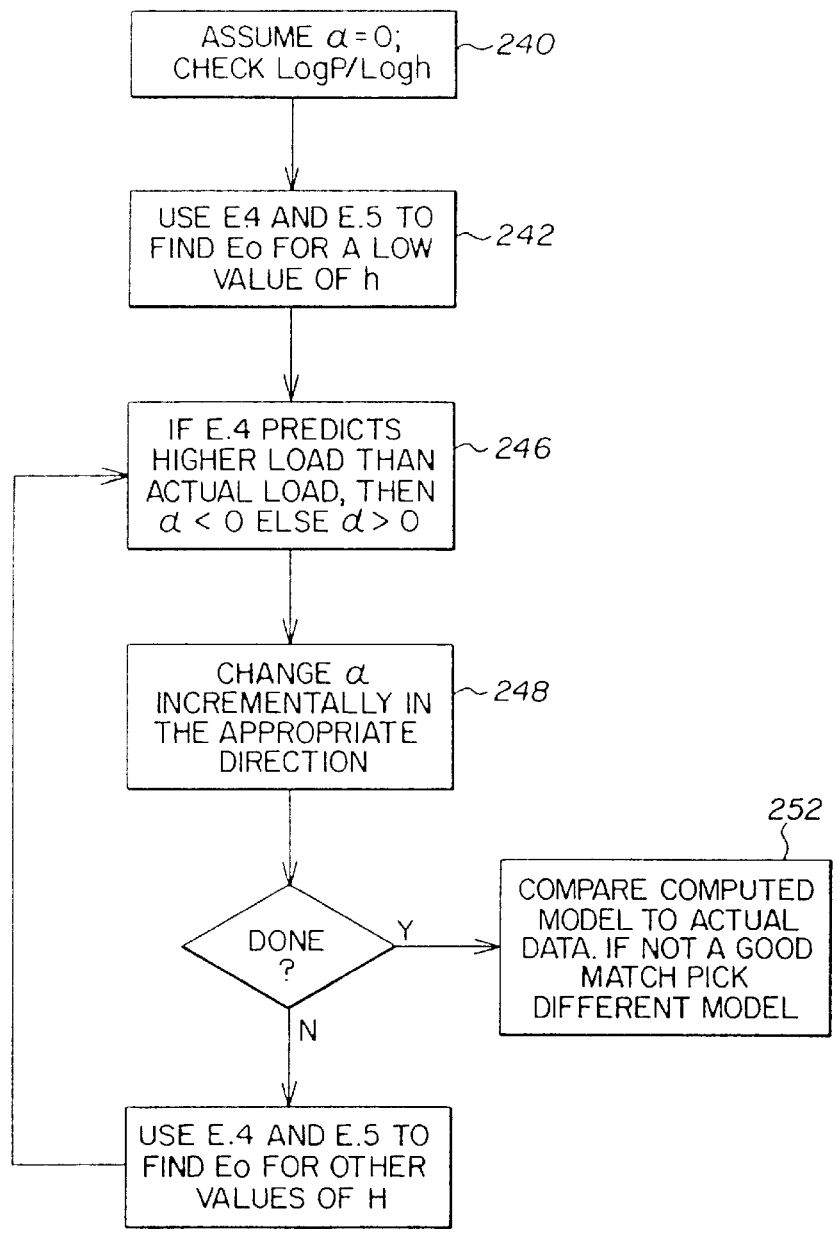
FIG. 10 is a flowchart describing how mechanical properties are determined using an exponential model, for a spherical indenter.
Figure 16:
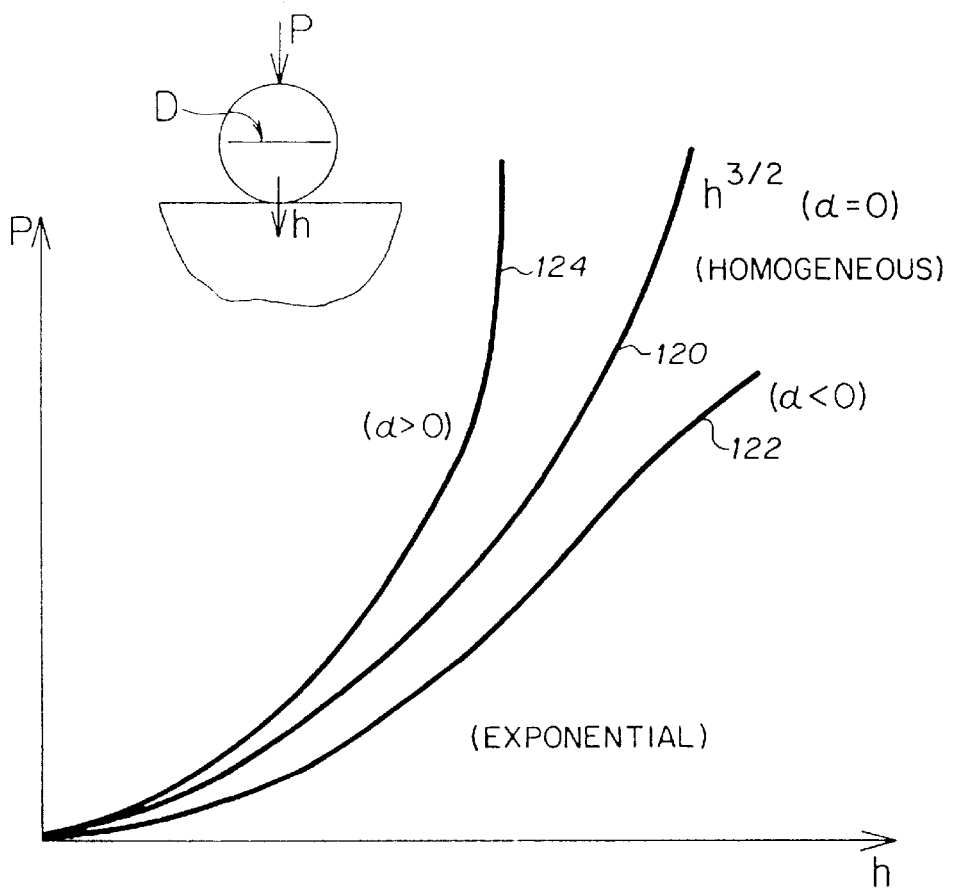
FIG. 16 is a diagram of a load/depth curve for an exponential model for a spherical indenter.

Referring now to FIG. 10, the determination of Young's modulus (Eo) and the variation α of a functionally graded material using a spherical indenter in a loading indentation test, and using the exponential model, will now be described. An example load/depth curve for this embodiment is shown in FIG. 16. The depth is on the abscissa while the load is on the ordinate. The spherical indenter has a diameter D. For homogeneous materials, as shown at 120, $P \sim h^{3/2}$. If α is less than zero, as shown at 122, the indenter displaces more material at the same load. If α is greater than zero, as shown at 124, the indenter displaces less material at the same load. One constraint of this test is that, for α>0, $P/(E_o D^2) < 0.37/(\alpha D)^3$. For α<0, $P/(E_0 D^2) < -0.24/(\alpha D)^3$.

The process begins by assuming that the variation is zero, in step 240 (FIG. 10). If logP/logh is about 3/2, then the variation is zero. Using Equations E.4 and E.5, in step 242 the value of Young's modulus at the surface is determined for a load P and depth h for a low value of the depth h from the measured load/depth curve. Using the initial Eo, and the value h from a second point on the load/depth curve, equation E.4 is used to predict a load P'. If the load P' is higher than the load P actually reported for the given depth h, as determined at step 246, then the variation α is less than zero. Otherwise, the variation α is greater than zero. The variation α is then varied in step 248 by a small factor Δα in the appropriate direction in order to make a better estimate. Steps 246 and 248 are used repeatedly to fit the load/depth and logP–logh curves to the exponential law model by determining appropriate values for the Young's modulus Eo and variation α. If the resulting fit is good, as determined by any appropriate similarity metric between the load/depth curve and the determined model, according to an a priori tolerance, in step 252, the process is complete, and the process returns to step 222 in FIG. 9. Otherwise, the power law model is used to develop a model, as is described in more detail below in connection with FIG. 13.

Figure 11:
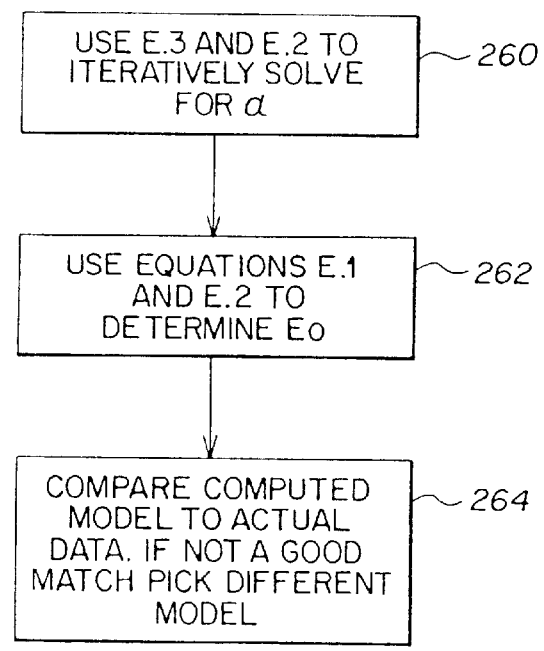
FIG. 11 is a flowchart describing how mechanical properties are determined using an exponential model, for a sharp or flat indenter.
Figure 17:
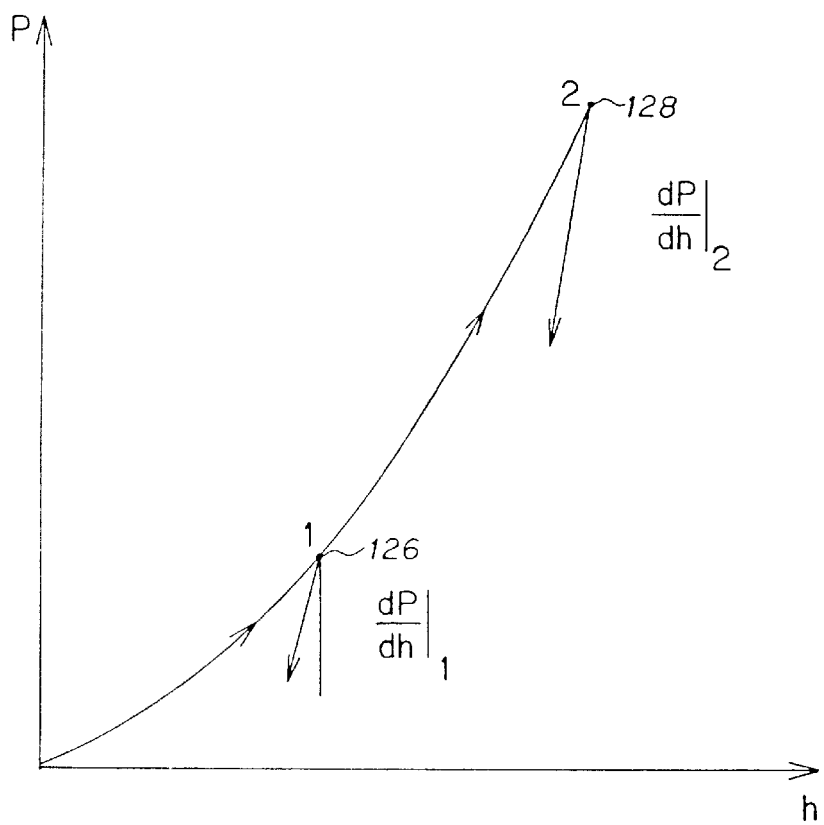
FIG. 17 is a diagram of a load/depth curve for an exponential model for a sharp or flat indenter.

Referring now to FIG. 11, the determination of Young's modulus (Eo) and the variation α of a functionally graded material using a sharp or flat indenter in an unloading indentation test, and using the exponential model, will now be described. An example load/depth curve for this embodiment is shown in FIG. 17. The depth is on the abscissa while the load is on the ordinate. In this test, the sample is loaded by the indenter up to a point, labeled 126. The sample is then unloaded, and the slope of the unloading curve is measured, as indicated by $dP/dh_1$. The sample is then loaded again by the indenter to a second point, labeled 128. The sample is then unloaded, and the slope of the unloading curve is measured, as indicated by $dP/dh_2$. The contact area A at points 126 and 128 also is measured. The equivalent radius a, used in equations below, is determined by: $a=\sqrt{A/\pi}$. One constraint of this test is that $-0.25<(a\alpha)<0.4$.

For this unloading test, first, in step 260, equations E.3 and E.2 are used to solve iteratively for the variation α. Equations E.1 and E.2 then are used to determine Eo step 262. If the resulting fit is good, as determined by any appropriate similarity metric between the load/depth curve and the determined model and a given a priori tolerance in step 264, the process is complete, and the process returns to step 222 in FIG. 8. Otherwise, the power law model is used to develop a model, as is described in more detail below in connection with FIG. 14.

Figure 12:
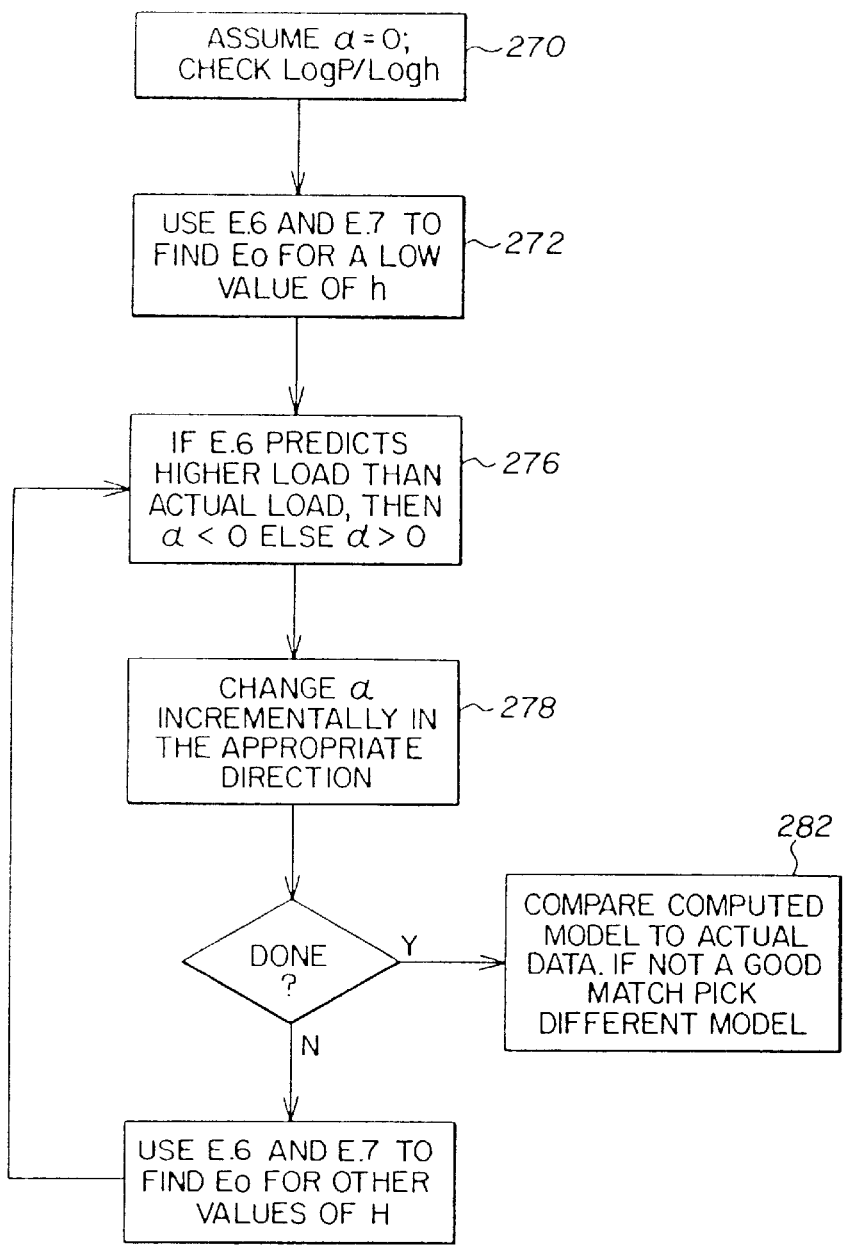
FIG. 12 is a flowchart describing how mechanical properties are determined using an exponential model, for a conical indenter.
Figure 18:
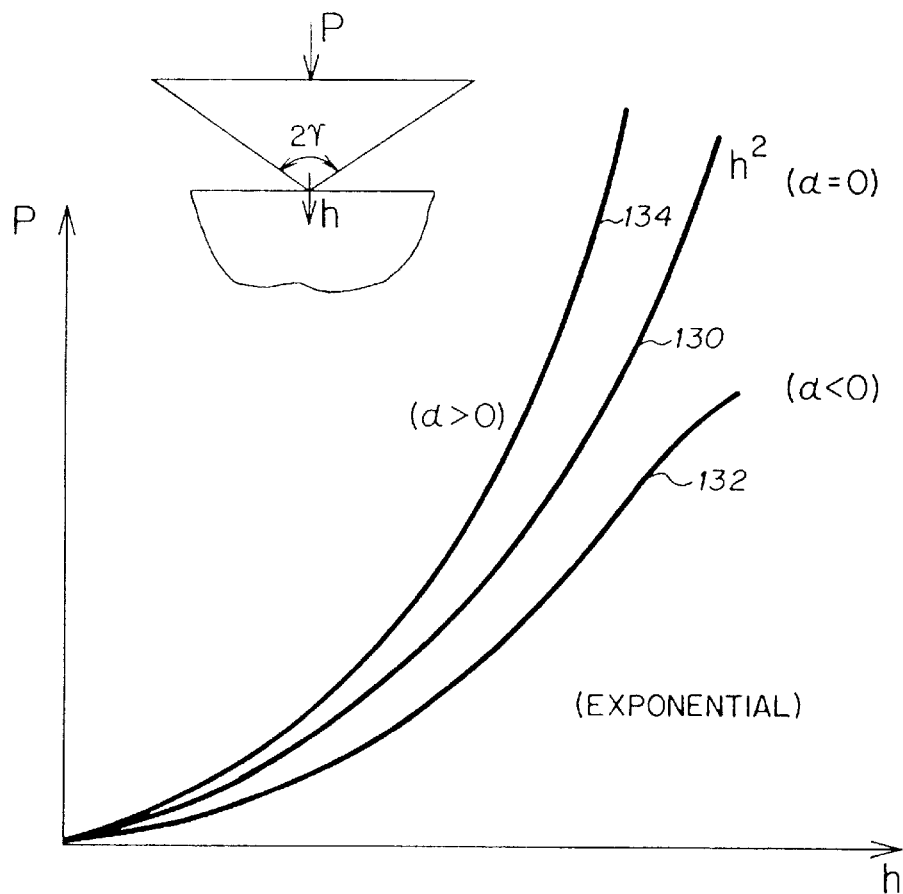
FIG. 18 is a diagram of a load/depth curve for an exponential model for a conical indenter.

Referring now to FIG. 12, the determination of Young's modulus (Eo) and the variation α of a functionally graded material using a conical indenter in a loading indentation test, and using the exponential model, will now be described. An example load/depth curve for this embodiment is shown in FIG. 18. The depth is on the abscissa while the load is on the ordinate. The conical indenter has an angle 2γ which defines the shape of the point. For homogeneous materials, as shown at 130, $P\sim h^2$. If α is less than zero, as shown at 132, the indenter displaces more material at the same load. If α is greater than zero, as shown at 134, the indenter displaces less material at the same load. One constraint of this test is that $-0.18<(a\alpha)<0.23$.

The process of FIG. 12 begins by assuming that the variation is zero, in step 270. If logP/logh is about 2, then the variation is zero. Using Equations E.6 and E.7, in step 272 the value of Young's modulus at the surface is determined for a load P and depth h for a low value of the depth h from the measured load/depth curve. Using the initial Eo, and the value h from a second point on the load/depth curve, equation E.6 is used to predict a load P'. If the load P' is higher than the load P actually reported for the given depth h, as determined at step 276, then the variation α is less than zero. Otherwise, the variation α is greater than zero. The variation α is then varied in step 278 by a small factor Δα in the appropriate direction in order to make a better estimate. Steps 276 and 278 are used repeatedly to fit the load/depth and logP–logh curves to the exponential law model by determining appropriate values for the Young's modulus Eo and variation α. If the resulting fit is good, as determined by any appropriate similarity metric between the load/depth curve and the determined model and a given a priori tolerance in step 282, the process is complete, and the process returns to step 222 in FIG. 8. Otherwise, the power law model is used to develop a model, as is described in more detail below in connection with FIG. 15.

The following equations are used to determine Eo and a using the exponential model: Equation E.1:

Equation E.1:

$$\frac{E_o}{1-v_o^2} = \frac{dP}{dh}\frac{\Psi}{\pi a}$$

Equation E.2:

$$\Psi = \frac{\pi}{2} - (a\alpha)\left(3.7 - 403.5\frac{(a\alpha)^2}{3} + 403.5^2\frac{2}{45\pi}(a\alpha)^5\right)$$

Equation E.3:

$$\frac{\Psi 1}{\Psi 2} = \frac{\left.\frac{dP}{dh}\right|^2}{\left.\frac{dP}{dh}\right|^1} \Rightarrow \alpha$$

Equation E4:

$$h = \frac{P}{\pi a E_o}\Psi + \frac{2a^2}{3D}\left(1 - \frac{4}{15}403.5(\alpha a)^3\right)$$

Equation E.5:

$$a^3 = \frac{3\pi P}{E_o}\left(\frac{8\pi}{D} + \frac{P}{E_o}403.5\alpha^3\right)^{-1}$$

Equation E.6:

$$P = \pi a^2 \frac{E_o}{1-v_o^2} \frac{\cot\gamma}{2\left(1 - \frac{807}{3\pi}(\alpha a)^3\right)}$$

Equation E.7:

$$h = a\cot\gamma\left[\frac{\Psi^{-1}}{4\left(1 - \frac{807}{3\pi}(\alpha a)^3\right)} + \frac{\pi}{4} - \frac{403}{12}(a\alpha)^3\right]$$

Equations E.6 and E.7 also can be used to determine the contact area of the conical indenter directly from the load/depth relationship. One constraint of this test if $-0.18<(a\alpha)<0.23$.

Figure 19:
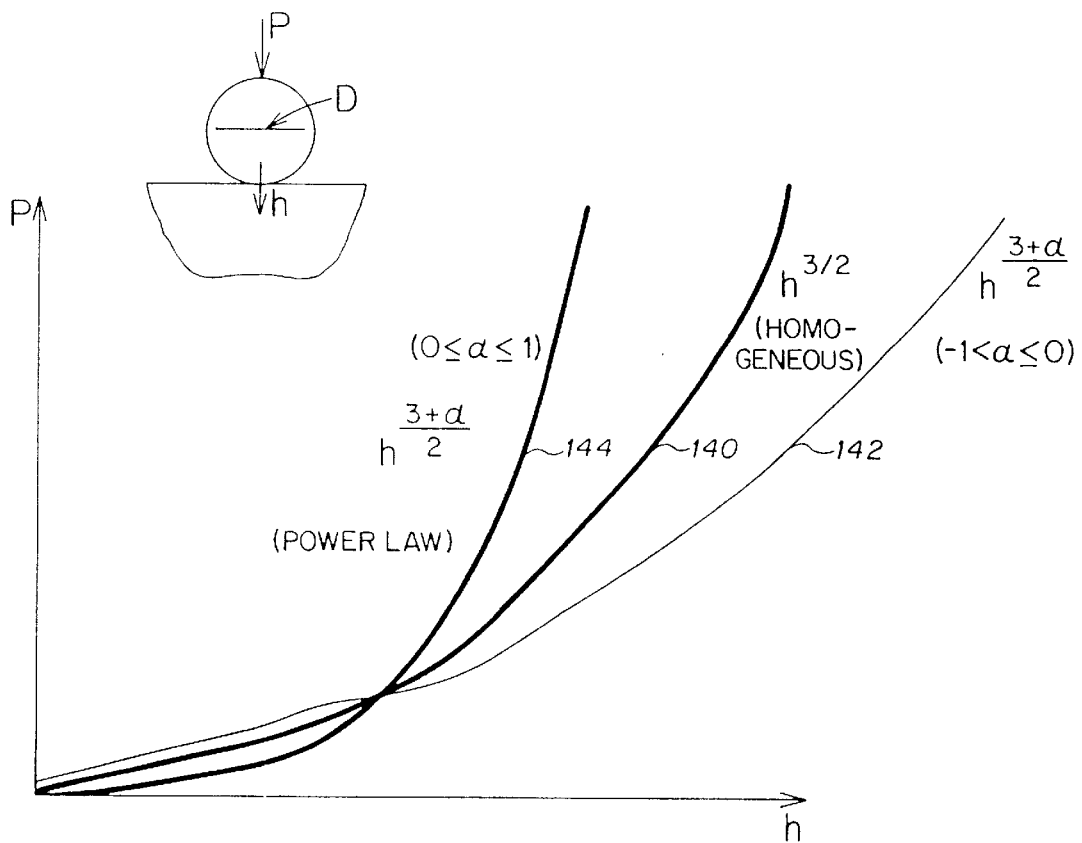
FIG. 19 is a diagram of a load/depth curve for a power law model for a spherical indenter.

Referring now to FIG. 13, the determination of Young's modulus (Eo) and the variation α of a functionally graded material using a spherical indenter in a loading indentation test, and using the power law model, will now be described. An example load/depth curve for this embodiment is shown in FIG. 19. The depth is on the abscissa while the load is on the ordinate. The spherical indenter has a diameter D. For homogeneous materials, as shown at 140, $P\sim h^{3/2}$. If α is less than zero, as shown at 142, the indenter displaces more material at the same load. If α is greater than zero, as shown at 144, the indenter displaces less material at the same load. One constraint of this test is that, for $-1<\alpha\leq 1$.

In this embodiment logP/logh is computed in step 290 in FIG. 13. Since this value should be about $(3+\alpha)/2$, an initial value for the variation α is determined. If the variation is zero, the material is homogeneous. The variation should have an absolute value less than one. Next, in step 292, equations P.4 and P.5 are used to fit the load/depth curve, to obtain the value of the Young's modulus Eo. These equations use equation P.1 for the value of the variable b. If the resulting fit is good, as determined by any appropriate similarity metric between the load/depth curve and the determined model and a given a priori tolerance in step 294, the process is complete, and the process returns to step 222 in FIG. 9. Otherwise, the material might not be capable of characterization by the power law or exponential models, or may not be graded in a way that enables characterization by these methods.

In this test, equations P.2 and P.3 do not use the contact area a. The contact area a, however, can be computed directly from the load/depth relationship using equation P.7.

Figure 14:
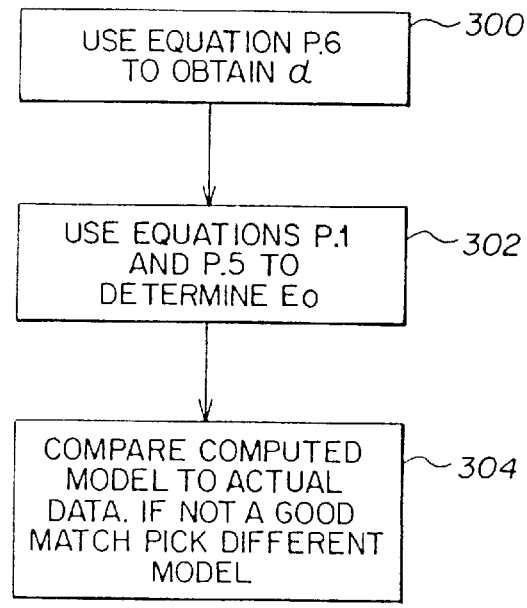
FIG. 14 is a flowchart describing how mechanical properties are determined using a power law model, for a sharp or flat indenter.
Figure 20:
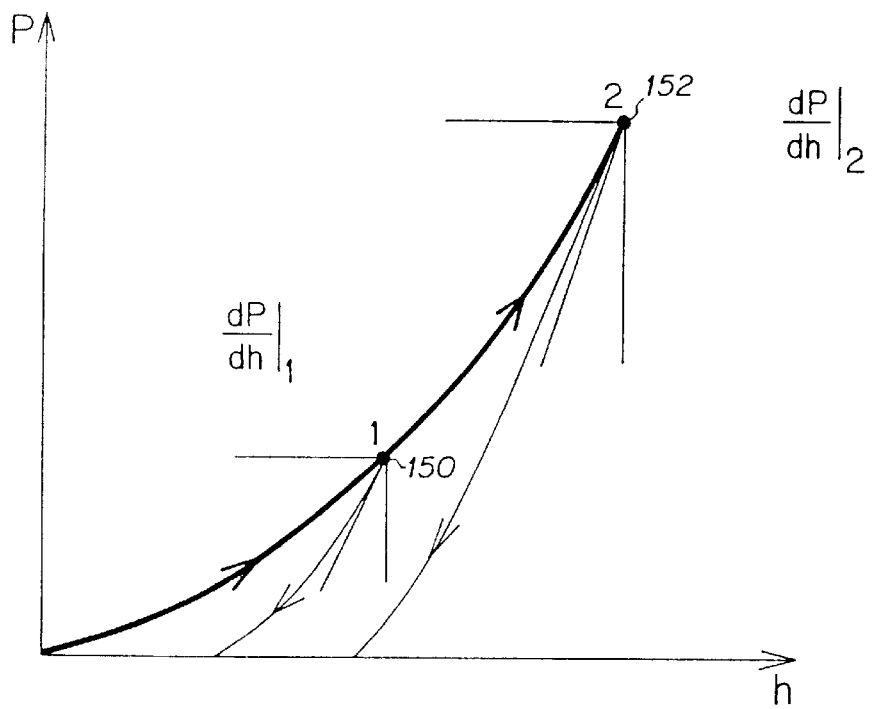
FIG. 20 is a diagram of a load/depth curve for a power law model for a sharp or flat indenter.

Referring now to FIG. 14, the determination of Young's modulus (Eo) and the variation α of a functionally graded material using a sharp or flat indenter in an unloading indentation test, and using the power law model, will now be described. An example load/depth curve for this embodiment is shown in FIG. 20. The depth is on the abscissa while the load is on the ordinate. In this test, the sample is loaded by the indenter up to a point, labeled 150. The sample is then unloaded, and the slope of the unloading curve is measured, as indicated by $dP/dh_1$. The sample is then loaded again by the indenter to a second point, labeled 152. The sample is then unloaded, and the slope of the unloading curve is measured, as indicated by $dP/dh_2$. The contact area A at points 150 and 152 also is measured. The equivalent radius a, used in equations below, is determined by: $a = \sqrt{A/\pi}$. One constraint of this test is that $-1 < \alpha \leq 1$.

The first step 300 of the process in FIG. 14 involves determining the variation α using equation P.6. Next, in step 302, equation P.5, and P.1 for the value b, are used to obtain the Young's modulus Eo. If the resulting fit is good, as determined by any appropriate similarity metric between the load/depth curve and the determined model and a given a priori tolerance in step 304, the process is complete, and the process returns to step 222 in FIG. 9. Otherwise, the material might not be capable of characterization by the power law or exponential models, or may not be graded in a way that enables characterization by these methods.

Figure 15:
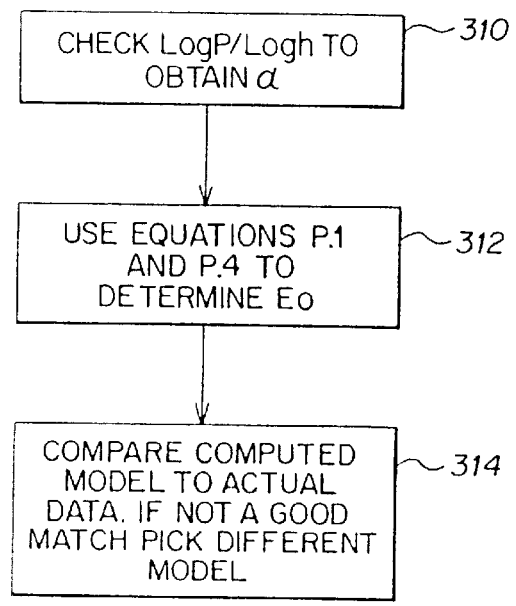
FIG. 15 is a flowchart describing how mechanical properties are determined using a power law model, for a conical indenter.
Figure 21:
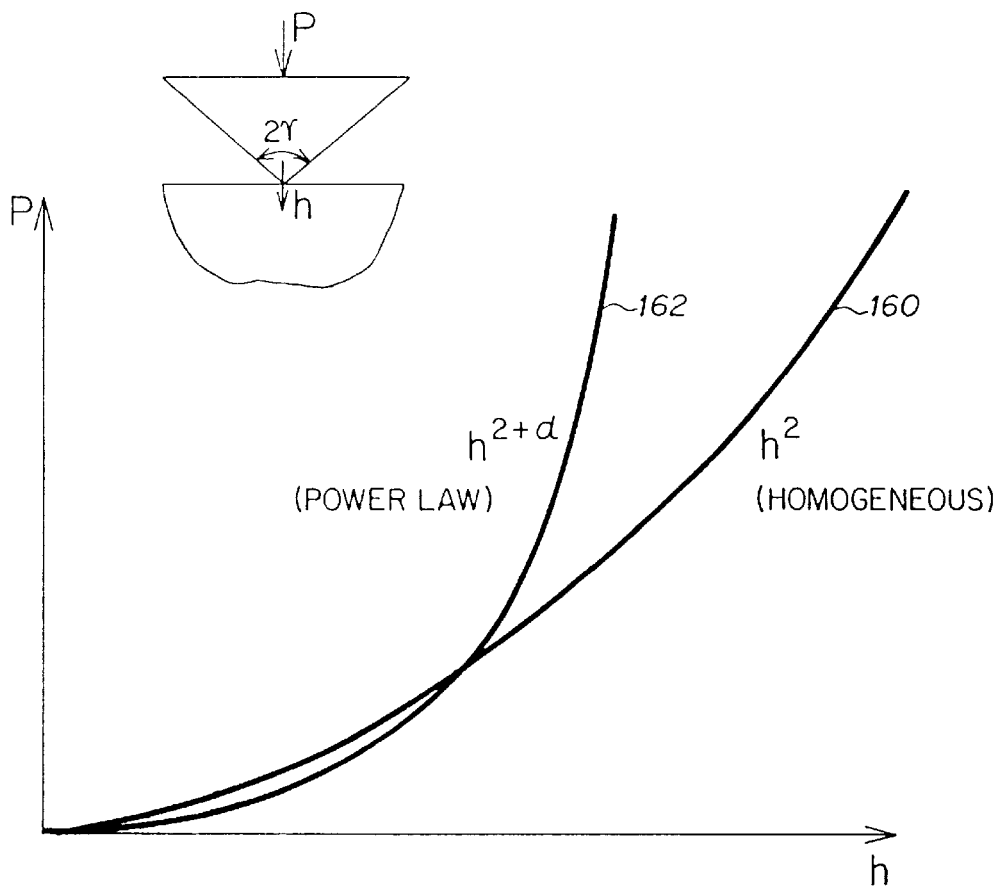
FIG. 21 is a diagram of a load/depth curve for a power law model for a conical indenter.

Referring now to FIG. 15, the determination of Young's modulus (Eo) and the variation α of a functionally graded material using a conical indenter in a loading indentation test, and using the power law model, will now be described. An example load/depth curve for this embodiment is shown in FIG. 21. The depth is on the abscissa while the load is on the ordinate. The conical indenter has an angle 2γ which defines the shape of the point. For homogeneous materials, as shown at 160, $P \sim h^2$. If α is greater than zero, as shown at 162, the indenter displaces less material at the same load. One constraint of this test is that $0 \leq \alpha \leq 1$.

In this process in FIG. 15, the logP/logh curve is first computed in step 310. Since this value should be about 2+α, an initial value for the variation α is determined. If the variation is zero then the material is homogeneous. The variation should be between greater than or equal to zero and less than one. Next, in step 312, equation P.4 is used to fit the load/depth curve, to obtain the value of the Young's modulus Eo. This equation uses equation P.1 for the value of the variable b. If the resulting fit is good, as determined by any appropriate similarity metric between the load/depth curve and the determined model and a given a priori tolerance in step 314, the process is complete, and the process returns to step 222 in FIG. 9. Otherwise, the material might not be capable of characterization by the power law or exponential models, or may not be graded in a way that enables characterization by these methods.

In this test, equations P.4 and P.1 do not use the contact area a. The contact area a, however, can be computed directly from the load/depth relationship using equation P.8.

The following equations are used to determine Eo and a using the power law model:

Equation P.1:

$$b = \sqrt{\left(1 - \frac{\alpha v_o}{1 - v_o}\right)(1 + \alpha)}$$

Equation P.2:

$$P = Ch^{(3+\alpha)/2}$$

Equation P.3:

$$C = \frac{E_o}{(1-v_o^2)} D^{\frac{1+\alpha}{2}} \frac{(1+\alpha)^{\frac{3+\alpha}{2}}}{(3+\alpha)} 2^{\frac{1-3\alpha}{2}} \frac{1}{b\sin\frac{b\pi}{2}} \frac{\Gamma\left(\frac{2+\alpha}{2}\right)}{\Gamma\left(\frac{1-\alpha}{2}\right)} \frac{\Gamma(2+\alpha)}{\Gamma\left(\frac{3+\alpha-b}{2}\right)\Gamma\left(\frac{3+\alpha+b}{2}\right)} \frac{1}{\Gamma\left(\frac{3+\alpha}{2}\right)\Gamma\left(\frac{1+\alpha}{2}\right)}$$

Equation P.4:

$$P = \frac{E_o}{(1-v_o^2)} \frac{(1+\alpha)^2 (2+\alpha)}{b\sin\frac{b\pi}{2}} (\tan\gamma)^{3+\alpha} h^{2+\alpha} \frac{\Gamma(2+\alpha)\left(\Gamma\left(1+\frac{\alpha}{2}\right)\right)^{2+\alpha}}{\Gamma\left(\frac{1-\alpha}{2}\right)\left(\Gamma\left(\frac{1+\alpha}{2}\right)\right)^{1+\alpha} \Gamma\left(\frac{3+\alpha-b}{2}\right)\Gamma\left(\frac{3+\alpha+b}{2}\right)}$$

Equation P.5:

$$\frac{dP}{dh} = \frac{E_o}{1-v_o^2} a^{(1+\alpha)} 2^{(1-\alpha)} \sqrt{\pi} \frac{\cos\alpha\frac{\pi}{2} \Gamma\left(1+\frac{\alpha}{2}\right)}{b\sin\frac{b\pi}{2} \Gamma\left(\frac{1+\alpha}{2}\right)} \frac{\Gamma(2+\alpha)}{\Gamma\left(\frac{3+\alpha+b}{2}\right)\Gamma\left(\frac{3+\alpha-b}{2}\right)}$$

Equation P.6:

$$\left(\frac{a_1}{a_2}\right)^{1+\alpha} = \frac{\left.\frac{dP}{dh}\right|_2}{\left.\frac{dP}{dh}\right|_1} \Rightarrow \alpha$$

Equation P.7:

$$a = \sqrt{\frac{hD(1+\alpha)}{2}}$$

Equation P.8:

$$h = a\frac{\sqrt{\pi}}{2\tan\gamma}\frac{\Gamma\left(\frac{1+\alpha}{2}\right)}{\Gamma\left(1+\frac{\alpha}{2}\right)}$$

After determining the Young's modulus and its spatial variation from the foregoing procedures, these values should be corrected to account for the stiffness of the indenter, as set forth in step 222 of FIGS. 8 and 9. In particular:

$$\frac{1-v_{spec}^2}{E_{spec}} = \frac{1-v_o^2}{E_o} - \frac{1-v_{ind}^2}{E_{ind}}$$

The function and advantage of these and other embodiments of the present invention will be more fully understood from the examples below. The following examples are intended to illustrate the benefits of the present invention, but do not exemplify the full scope of the invention.

EXAMPLES

The theory and numerical simulations for spherical indentation were checked with indentation experiments conducted on two different compositionally graded materials: (i) a sintered γ-TiAl/Y-TZP (yttria-stabilized tetragonal zirconia polycrystal) composite and (ii) a plasma sprayed Ni—$Al_2O_3$ Composite.

1. γ-TiAl/Y-TZP

A graded material was manufactured by sintering γ-TiAl/Y-TZP powders (50 at.% Al), 10 μm in particle size mixed with 3 mol % Y-TZP, to full density. A stepwise gradient in composition was produced by stacking 10 layers of different mixtures of the γ-TiA and Y-TZP powders. Sintering was carried out at 1200° C. in vacuum under 200 MPa of uniaxial pressure for 2 h. Subsequently, the material was cooled to room temperature at about 4° C./s . The calculation of E(z) through the thickness of the graded layer is based on the rule of mixtures. ($E(z)=c(z)E_{surf}+(1-c(z))E_{subs}$; c(z) is the volume fraction of the constituent phase at the indented surface of the graded layers, $E_{surf}$ is Young's modulus at the indented surface, and $E_{subs}$ is Young's modulus of the homogeneous substrate) The value of E was taken as 170 GPa for γ-TiAl and 210 GPa for Y-TZP. Homogeneous γ-TiAl and Y-TZP materials were also processed by employing the procedures identical to those of the graded composites, in order to compare their indentation responses on a common basis.

2. Ni—$Al_2O_3$

The Ni—$Al_2O_3$ graded material was produced by feeding a controlled mixture of Ni and $Al_2O_3$ powders into a plasma torch. Rotating Ni substrates in plate form, 5 cm×3 cm×4 mm, were used to deposit the graded layers in air at atmospheric pressure. E is taken as 214 GPa for Ni, 380 GPa for the sintered $Al_2O_3$, and 62 GPa for the plasma-sprayed alumina. As a first approximation, E for plasma-sprayed Ni is considered to be similar to that of dense Ni. This is in agreement with microstructural observations on graded plasma-sprayed materials conducted in the present work. These observations showed that Ni particles were fully dense in contrast to $Al_2O_3$ particles which were strongly microcracked. Hence, the influence of the plasma spray processing on E, as measured under compressive loads, was assumed to arise mainly in $Al_2O_3$ rather than in Ni coatings.

3. Experimental Methods

Careful grinding and polishing were done to remove the substrates of the FGMs so that indentation experiments could be performed at the commencement or end of the gradient layer. In order to compare the indentation response of the homogeneous (dense) Ni to that of the graded Ni—$Al_2O_3$ at the 100% pure Ni surface, experiments on the graded layer were conducted on the dense substrate rather than on plasma-sprayed Ni. In addition, the surfaces of the graded materials containing a thin layer of homogeneous $Al_2O_3$ or Y-TZP were ground so that the indentation experiments could be conducted on the graded material. All surfaces to be indented were finally polished using a 1-μm diamond paste.

Indentation experiments were conducted with the new device built to enable in-situ and accurate measurements of load and indentation depth for applied loads and displacements in the range 0.3 N–200 N and 0.1 μm–200 μm, respectively. The resolution of the measured load and indentation depth were ±0.01 μm, respectively. All experiments were conducted with a WC spherical indenter of diameter 1.59 mm. The maximum loading and unloading rates were set as 0.01 μm/s and 0.005 μm/s, respectively.

4. Experimental Results and Comparison with Theory.

Before comparing the experiments with theory, it is appropriate to ensure that the key test parameters and the input to the theory are mutually consistent. For the homogeneous γ-TiAl/Y-TZP and ceramics with high E values, it is important to account for the compliance of the indenter. For comparison with the experimentally obtained P-h curves, the Hertzian results for homogeneous materials was therefore modified to include possible elastic deformation of the indenter itself, as follows:

$$P = \frac{2\sqrt{2D}\cdot Kh^{1.5}}{3}\left\{1+\left[\frac{2(1-v_{ind}^2)}{KE_{ind}}\right]^{\frac{2}{3}}\right\}^{-3/2}, K = \frac{1-v_{ind}^2}{E_{ind}} + \frac{1-v_{spec}^2}{E_{spec}}.$$

Here $E_{ind}$ is Young's modulus of the WC spherical indenter (=614 GPa), $v_{ind}$ is the Poisson ratio of the indenter (=0.22), D is the diameter of the indenter (=1.59 mm), and $E_{spec}$ and $v_{spec}$ are Young's modulus and Poisson ratio, respectively, of the specimen. In order to account for the possible deformation of the indenter, the following procedure was employed for the graded materials. (a) The P-h relation for the graded material was compared to that of the homogeneous material; the elastic properties of the homogeneous materials are those of the indented surface of the graded layer. (b) For a given h, the ratio of the applied load for the graded material to that of the homogeneous material was calculated. This step was repeated for a number of points in the P-h curve. (c) The equation above was multiplied by the ratio from step (b) in order to obtain the P-h response of the graded material, which accounts for the indenter deformation. In all calculations, the through-thickness variation of Young's modulus is given by an exponential model. The Poisson ratio was assumed constant ($\nu=0.3$) through the thickness of the graded layer.

5. Homogeneous and Graded γ-TiAl/Y-TZP

Figure 22:
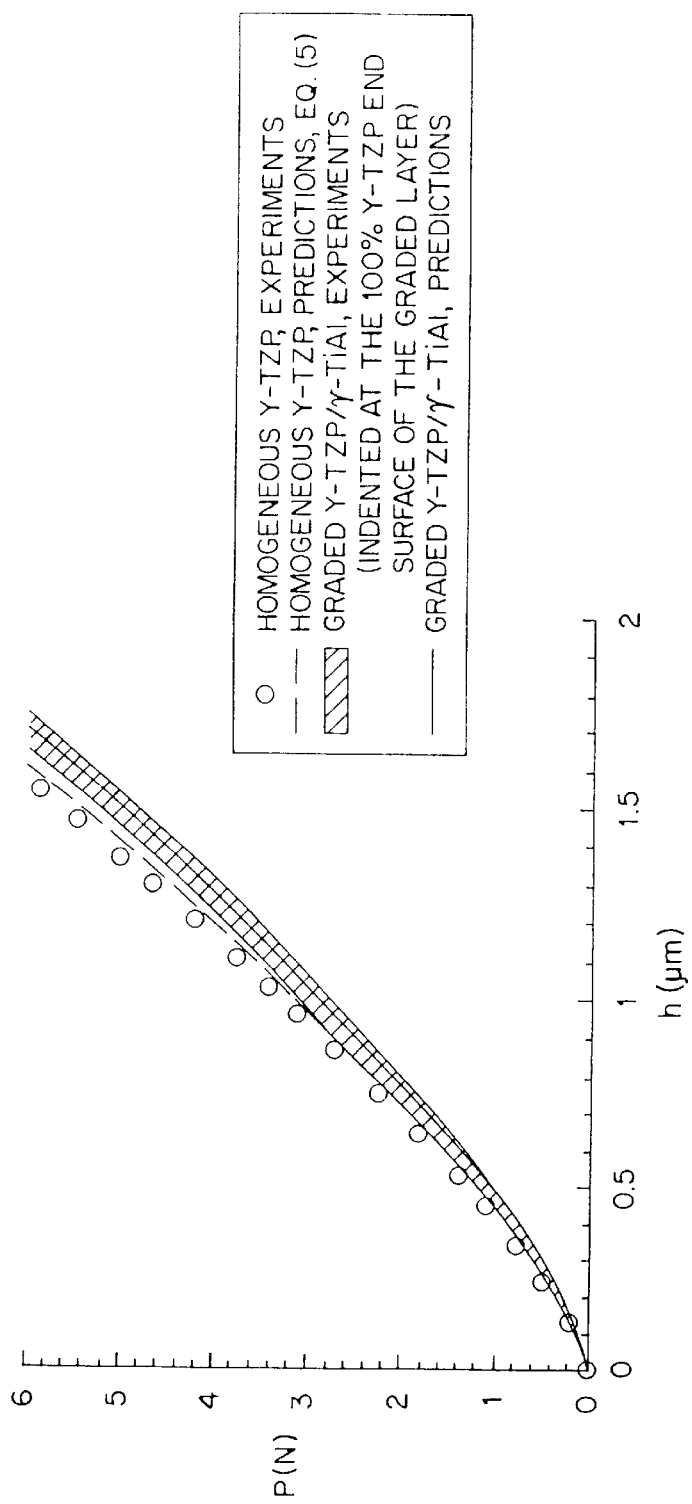
FIG. 22 is a graph comparing experimental results with theoretical results for graded Y-TZP/γ-TiAl and homogeneous Y-TZP.

FIG. 22 shows the P-h curves measured in a homogeneous surface layer of Y-TZP produced during the processing of γ-TiAl/Y-TZP, as well as the P-h response determined on the 100% Y-TZP end of this graded material. As E for Y-TZP is only of about 18% higher than that of γ-TiAl, the P-h curve of the graded material is expected to be only slightly shifted to lower values of load in relation to the curve of the homogeneous Y-TZP. The good agreement between theoretical and experimental results is evident in FIG. 22.

Figure 23:
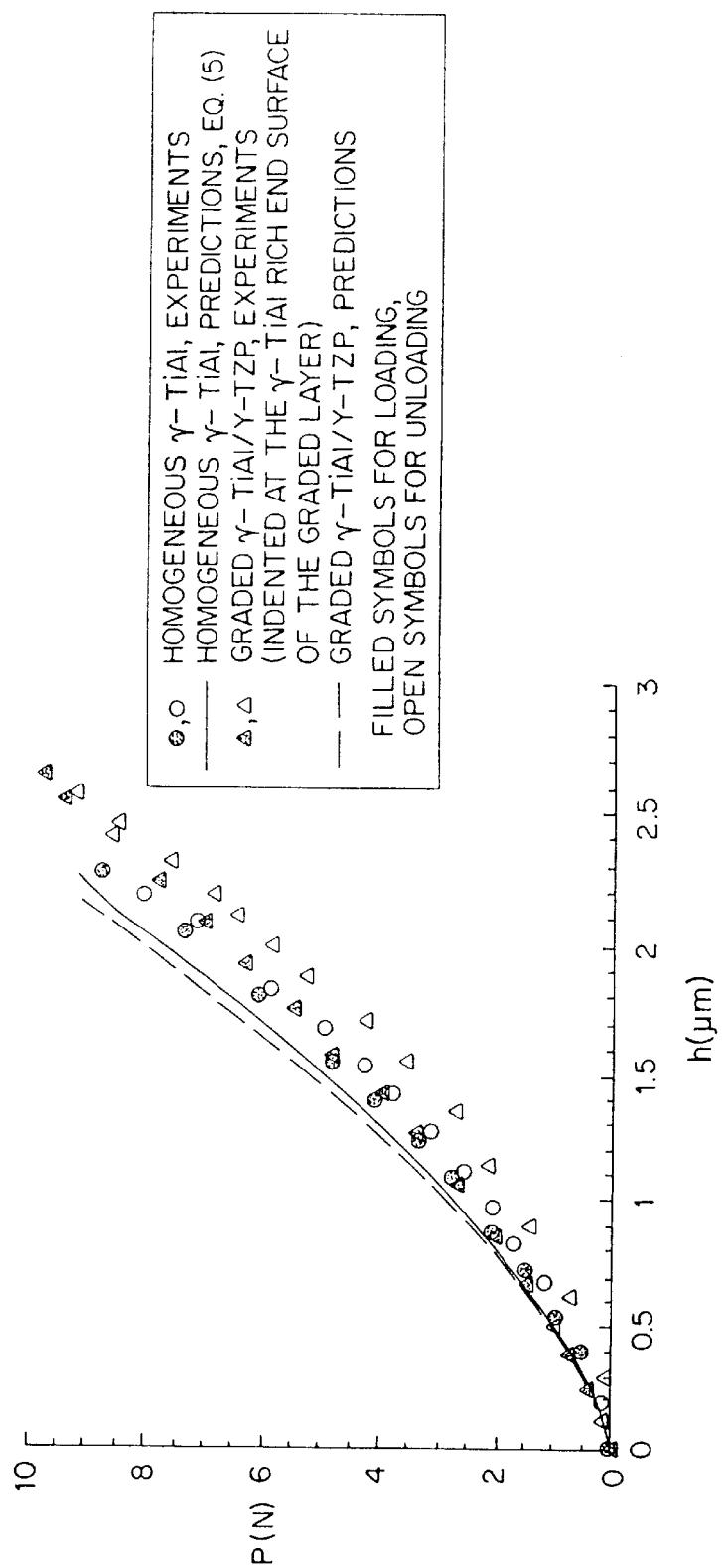
FIG. 23 is a graph comparing experimental results with theoretical results for graded γ-TiAl/Y-TZP and homogeneous y-TiAl.

FIG. 23 shows the results of the indentation experiments conducted on γ-TiAl/Y-TZP, indented on the TiAl-rich side of the graded layer, along with those of the homogeneous γ-TiAl. The predictions of the theory are also plotted for this case. Since Y-TZP has a larger value of E than γ-TiAl, the P-h curve for the graded material is expected to be shifted to higher values of load than that of the homogeneous γ-TiAl. Nevertheless, the opposite trend is determined experimentally, i.e., the P-h curve of γ-TiAl lies on top of that of the FGM. The only factor that could eventually produce such an effect would be the development of plasticity when indenting the graded material. This would shift the P-h curve to lower values of load and produce a residual imprint on the indented surface. Hence, the P-h curve on unloading will differ from that measured on loading. As shown in FIG. 23, such an inelastic behavior indeed occurs in the graded material. In this sense, the maximum residual indentation depth measured in the P-h loop of the γ-TiAl/Y-TZP is about 0.24 μm in comparison with 0.12 μm for the homogeneous γ-TiAl or Y-TZP. These values are the average of four different indentation tests in each material; the experimental scatter of this measurement was of about ±0.02 μm.

The residual imprints obtained at 50 N of maximum load also indicated the aforementioned larger inelastic response of γ-TiAl/Y-TZP in comparison with homogeneous γ-TiAl. The diameter of the impressions in the graded material seen on the surface are about 15% larger than in the homogeneous intermetallic (for the same maximum load). Furthermore, the imprints obtained in γ-TiAl, are shallower than those of the graded material. This trend was also confirmed for a maximum load of 20 N. Interestingly, such an enhancement of inelastic response for γ-TiAl/Y-TZP on the surface cannot be associated with deformation of Y-TZP particles as the residual imprint size of homogeneous Y-TZP is even smaller and shallower than that of the homogeneous γ-TiAl.

From numerical simulations, the enhancement of near-surface plasticity in γ-TiAl/Y-TZP is a particular effect expected when indenting exponential gradients where E increases with depth, and the present experimental results are in good agreement with the theory. In addition to gradient shape, another aspect that can induce plasticity in the present graded materials is a residual tensile stress field at the indented surface due to cooling from sintering temperature. However, as calculated in the present work, residual compressive stresses are expected to develop at the indented surfaces of γ-TiAl/Y-TZP. This analysis was done using the general purpose finite element code ABAQUS, version 5.3, available from Hibbit, Karlsson and Sorenson, Inc., Providence, R.I. The axisymmetric models were analyzed within the context of thermo-elasticity. The actual geometry of the indented specimens was modeled. The thermal expansion coefficients of the Y-TZP and γ-TiAl constituent phases were taken as $10 \times 10^{-6}$ and $15 \times 10^{-6}$, respectively. The material was regarded as being free of residual stresses at the sintering temperature. Hence, this factor is not likely to lead to the observed trends.

6. Homogeneous and Graded Ni—$Al_2O_3$

Figure 24:
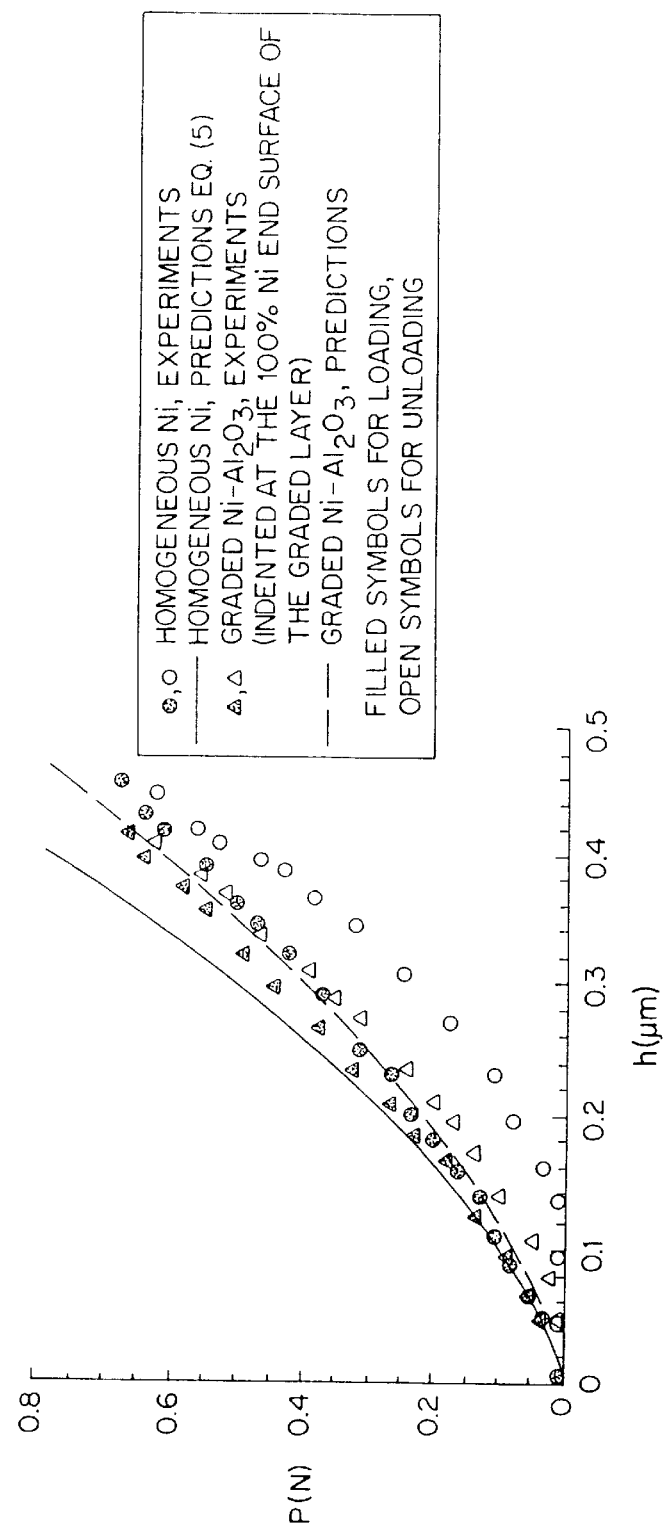
FIG. 24 is a graph comparing experimental results with theoretical results for graded Ni-$Al_2O_3$ and homogeneous Ni.

FIG. 24 compares the P-h response of the graded Ni—$Al_2O_3$ indented on the pure Ni side with that of homogeneous Ni. On loading, the P-h relation measured with the homogeneous material is shifted slightly to lower values of load. In addition, it is worth noting that the residual depth upon fully unloading for the homogeneous nickel is twice that of the graded composite. These results indicate that even for a maximum load of about 0.7 N and for spherical indentation, plasticity clearly develops in the homogeneous metal, and that such a plastic behavior is greatly reduced for the graded material due to the presence of alumina particles underneath the indented surface. When indenting the Ni—$Al_2O_3$ graded material from the alumina side, shown in FIG. 25, a residual depth is also observed; this seems to indicate that plastic deformation occurs at the nickel particles below the indented surface. These results are evident even for loads as low as 0.7 N.

Figure 25:
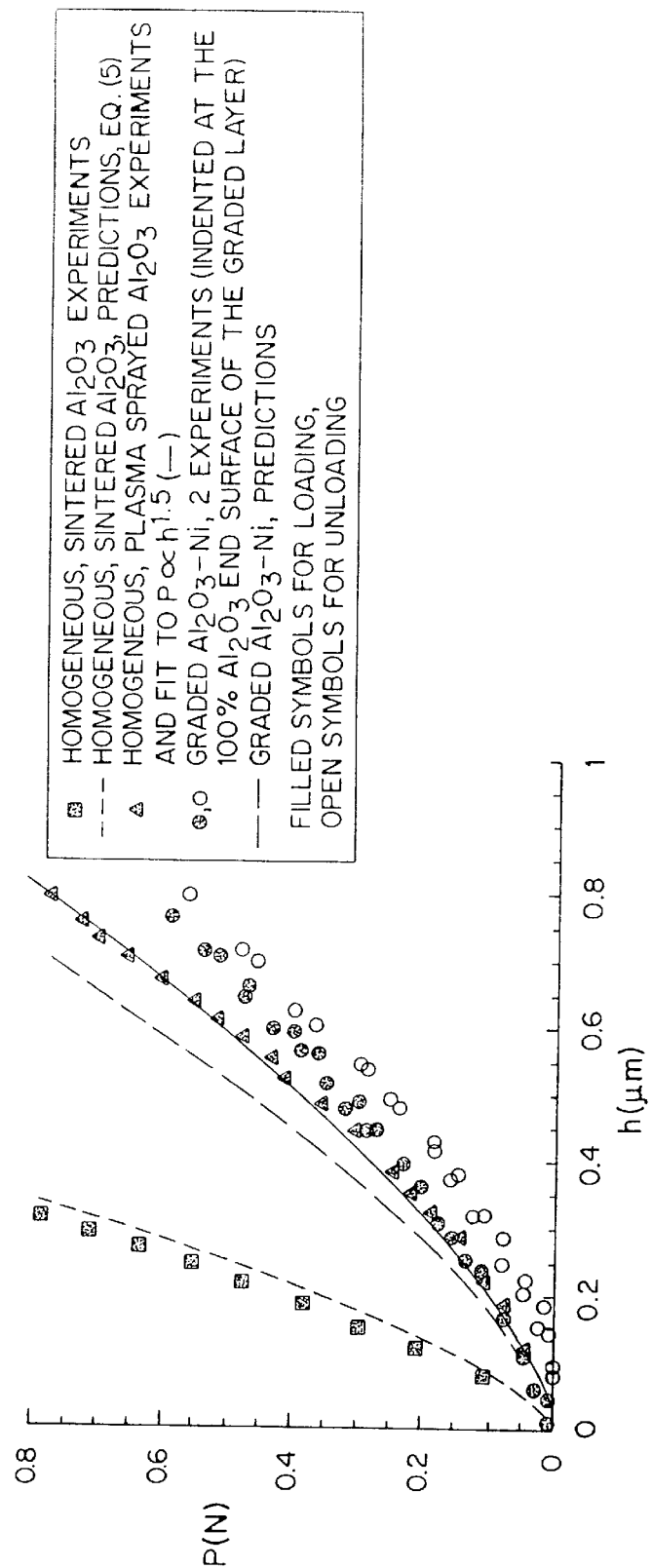
FIG. 25 is a graph comparing experimental results with theoretical results for graded $Al_2O_3$-Ni and homogeneous $Al_2O_3$.

It is also seen in FIG. 25 that E for plasma-sprayed $Al_2O_3$ can be estimated from the above equation. The validity of such an approach is justified by the result that experimental data conform to the well known relationship, $P h^{1.5}$, for the homogeneous, plasma-sprayed $Al_2O_3$. It can be inferred from FIG. 25 and this equation that E for plasma-sprayed $Al_2O_3$ is 52±10 GPa. This value, as anticipated, is substantially lower than the E for fully dense $Al_2O_3$ (≈350 GPa). The present results of E for thermally-sprayed $Al_2O_3$ are in the same range of values reported by others who employed different techniques for ceramic materials.

The above results are complemented with the residual imprints. The imprint size and the amount of plasticity which spreads out of the imprint are reduced when indenting the graded material from the nickel side. These observations can be related well with the analytical results for a graded material whose E value decreases exponentially with depth. Furthermore, finite element results indicate that plasticity is suppressed in the graded material as the Mises isostress contours are more confined in this case). Such a confinement cannot be achieved when a homogeneous layer of the material with the highest E is placed on top of the more compliant material with thickness similar to the contact radius of the indenter. Therefore, in view of the experimental and theoretical results, the reduction in the lateral spread of plasticity seems to be a particular feature of the indentation response of graded materials whose E value decreases exponentially with depth.

Another possible explanation for the confinement of plasticity evolution in the Ni—$Al_2O_3$ graded material, as indented from the Ni side, is the strain hardening change with depth. The $Al_2O_3$ particles are expected to strain harden the pure Ni (due to constraint) in proportion to their concentration. Therefore, the strain hardening should increase with depth. This will clearly result in less overall plastic deformation which will be reflected in the P-h curves. However, the gradation in strain hardening cannot explain the experimentally observed lowering of plasticity developed at the Ni surface of the graded material (compared to homogeneous Ni). Since the variation of the strain hardening exponent within the plastic zone is small, its effect on the imprint size can be disregarded. It can thus be concluded that the overall response is due primarily to the gradient in E and not to the gradation in strain hardening.

Those skilled in the art would readily appreciate that all parameters listed herein are meant to be exemplary and that actual parameters will depend upon the specific application for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A process for generating digital information indicative of a measure of variation of a mechanical property of a material, comprising:
   receiving signals indicative of a load/depth relationship from an indentation test for at least two depths of an indenter applied to the material;
   receiving signals indicative of the geometry and properties of the indenter and a Poisson ratio of the material; and
   computing the variation in the mechanical property as a function of the load/depth relationship, the geometry of the indenter, and the Poisson ratio.

2. The process of claim 1, wherein the variation is essentially zero and the material is a homogeneous material.

3. The process of claim 1, wherein the variation is non-zero and the material is a functionally-graded material.

4. The process of claim 3, wherein computation makes use of a known reference value of the mechanical property at a reference location in the sample.

5. The process of claim 1, wherein the mechanical property is elastic modulus.

6. A process for measuring a mechanical property of a functionally-graded material, comprising:
   receiving signals indicative of a load/depth relationship of an indentation test for at least two depths of an indenter applied to the material;
   receiving signals indicative of the geometry and properties of the indenter and a Poisson ratio of the material; and
   computing the mechanical property as a function of the load/depth relationship, the geometry of the indenter, and the Poisson ratio.

7. A process as in claim 6, further comprising computing the variation in the mechanical property as a function of depth, geometry, and Poisson ratio of the sample.

8. A process as in claim 7, wherein computation makes use of a known reference value of the variation in the mechanical property.

9. A process for detecting a deviation from a variation in a mechanical property of a material as a function of depth, comprising:
   receiving signals indicative of a load/depth relationship of an indentation test for a depth of an indenter applied to the material;
   receiving signals indicative of the geometry of the indenter and a Poisson ratio of the material;
   computing a load/depth relationship according to the geometry and properties of the indenter, the Poisson ratio, and the variation in the mechanical property and a reference mechanical property; and
   comparing the computed load/depth relationship to the received signal to detect the deviation.

10. A process as in claim 9, wherein the variation is known.

11. A process as in claim 9, further comprising determining the variation by computing the variation in the mechanical property as a function of the load/depth relationship, the geometry of the indenter, and the Poisson ratio.

12. A process as in claim 11, further comprising computing the reference mechanical property as a function of the load/depth relationship, the geometry of the indenter, and the Poisson ratio.

13. A process as in claim 9, further comprising computing the reference mechanical property as a function of the load/depth relationship, the geometry of the indenter, and the Poisson ratio.

14. A method comprising:
   performing an indentation test on a sample with an indenter in a direction essentially parallel to a direction of gradation of a functionally-graded material and deriving and recording a relationship between the load applied to the indenter and the depth of penetration of the indenter into the sample.

15. A computer system for generating digital information indicative of a measure of variation of a mechanical property of a material, comprising:
   means for receiving signals indicative of a load/depth relationship from an indentation test for at least two depths of an indenter applied to the material;
   means for receiving signals indicative of the geometry and properties of the indenter and a Poisson ratio of the material; and
   means for computing the variation in the mechanical property as a function of the load/depth relationship, the geometry of the indenter, and the Poisson ratio.

16. The computer system of claim 15, wherein the variation is essentially zero and the material is a homogeneous material.

17. The computer system of claim 15, wherein the variation is non-zero and the material is a functionally-graded material.

18. The computer system of claim 17, wherein computation makes use of a known reference value of the mechanical property at a reference location in the sample.

19. The computer system of claim 15, wherein the mechanical property is elastic modulus.

20. A computer system for measuring a mechanical property of a functionally-graded material, comprising:
   means for receiving signals indicative of a load/depth relationship of an indentation test for at least two depths of an indenter applied to the material;
   means for receiving signals indicative of the geometry and properties of the indenter and a Poisson ratio of the material; and
   means for computing the mechanical property as a function of the load/depth relationship, the geometry of the indenter, and the Poisson ratio.

21. A computer system as in claim 20, further comprising computing the variation in the mechanical property as a function of depth, geometry, and Poisson ratio of the sample.

22. A computer system as in claim 21, wherein computation makes use of a known reference value of the variation in the mechanical property.

23. A computer system for detecting a deviation from a variation in a mechanical property of a material as a function of depth, comprising:
   means for receiving signals indicative of a load/depth relationship of an indentation test for a depth of an indenter applied to the material;

means for receiving signals indicative of the geometry of the indenter and a Poisson ratio of the material;

means for computing a load/depth relationship according to the geometry and properties of the indenter, the Poisson ratio, and the variation in the mechanical property and a reference mechanical property; and means for comparing the computed load/depth relationship to the received signal to detect the deviation.

24. A computer system as in claim 23, wherein the variation is known.

25. A computer system as in claim 23, further comprising means for determining the variation by computing the variation in the mechanical property as a function of the load/depth relationship, the geometry of the indenter, and the Poisson ratio.

26. A computer system as in claim 25, further comprising means for computing the reference mechanical property as a function of the load/depth relationship, the geometry of the indenter, and the Poisson ratio.

27. A computer system as in claim 23, further comprising means for computing the reference mechanical property as a function of the load/depth relationship, the geometry of the indenter, and the Poisson ratio.

* * * * *

UNITED STATES PATENT AND TRADEMARK OFFICE

CERTIFICATE OF CORRECTION

PATENT NO. : 5,999,887

DATED : December 7, 1999

INVENTORS : Antonios E. Giannakopoulos, et al.

It is certified that an error appears in the above-identified patent and that said Letters Patent is hereby corrected as shown below:

Column 1, line 11, after "Energy" insert the following: --and Grant Number NOOO14-94-1-0139 awarded by the U.S. Department of the Navy--.

Signed and Sealed this

Twelfth Day of September, 2000

Attest:

Q. TODD DICKINSON

*Attesting Officer*      *Director of Patents and Trademarks*